(12) United States Patent
Strauss et al.

(10) Patent No.: US 8,512,311 B2
(45) Date of Patent: Aug. 20, 2013

(54) AUGMENTATION OF INTRALUMINAL MICROVESSEL FORMATION TO FACILITATE GUIDE WIRE CROSSING IN CHRONIC TOTAL OCCLUSIONS

(76) Inventors: Bradley H. Strauss, Toronto (CA); Amit Segev, Raanana (IL)

(*) Notice: Subject to any disclaimer, the term of this patent is extended or adjusted under 35 U.S.C. 154(b) by 742 days.

(21) Appl. No.: 11/606,040

(22) Filed: Nov. 30, 2006

(65) Prior Publication Data

US 2007/0154555 A1   Jul. 5, 2007

Related U.S. Application Data

(63) Continuation-in-part of application No. PCT/CA2005/001838, filed on Dec. 2, 2005.

(60) Provisional application No. 60/632,267, filed on Dec. 2, 2004.

(51) Int. Cl.
 *A61M 31/00*  (2006.01)

(52) U.S. Cl.
 USPC ............ 604/522; 604/500; 604/507; 604/506

(58) Field of Classification Search
 USPC ................... 604/500, 507–508, 522
 See application file for complete search history.

(56) References Cited

U.S. PATENT DOCUMENTS

| | | | | |
|---|---|---|---|---|
| 5,941,868 A | * | 8/1999 | Kaplan et al. ................ | 604/500 |
| 6,044,845 A | * | 4/2000 | Lewis ........................... | 128/898 |
| 6,149,641 A | * | 11/2000 | Ungs ............................ | 604/501 |
| 6,152,141 A | * | 11/2000 | Stevens et al. ............... | 128/898 |
| 6,436,087 B1 | * | 8/2002 | Lewis et al. .................. | 604/508 |
| 6,569,129 B1 | * | 5/2003 | Holmes et al. ................ | 604/264 |
| 6,660,034 B1 | | 12/2003 | Mandrusov et al. | |
| 7,326,238 B1 | * | 2/2008 | Kilpatrick et al. .......... | 623/1.13 |
| 7,758,636 B2 | * | 7/2010 | Shanley et al. .............. | 623/1.42 |
| 2003/0055445 A1 | * | 3/2003 | Evans et al. .................. | 606/159 |
| 2005/0079161 A1 | * | 4/2005 | Alt ............................... | 424/93.7 |
| 2005/0090748 A1 | * | 4/2005 | Makower et al. ............ | 600/467 |
| 2007/0173784 A1 | * | 7/2007 | Johansson et al. .......... | 604/507 |
| 2008/0118928 A1 | * | 5/2008 | Hageman ..................... | 435/6 |
| 2008/0200896 A1 | * | 8/2008 | Shmulewitz et al. ........ | 604/500 |

FOREIGN PATENT DOCUMENTS

| | | |
|---|---|---|
| WO | WO 03/028756 A | 4/2003 |
| WO | WO2004/043509 A | 5/2004 |
| WO | 2006/058434 | 6/2006 |

OTHER PUBLICATIONS

International Search Report, issued by ISA (Canadian Patent Office on International Patent Application No. PCT/CA2005/001838, completed Mar. 7, 2006.

Written Opinion, issued by ISA (Canadian Patent Office on International Patent Application No. PCT/CA2005/001838, completed Mar. 17, 2006.

(Continued)

*Primary Examiner* — Laura A Bouchelle
*Assistant Examiner* — Ian Holloway

(57) ABSTRACT

Method of preparing a clogged animal vessel, e.g. chronic total occlusion of an artery so as to be capable of crossing by a guidewire of an intraluminal device, e.g., angioplasty balloon. The method includes delivering an angiogenic agent to the occlusion site to promote angiogenesis within the occlusion to increases susceptibility to crossing.

29 Claims, 29 Drawing Sheets

(56) References Cited

OTHER PUBLICATIONS

Nikol, S. et al. Local perivascular application of low amounts of a plasmid encoding for vascular endothelial growth factor (VEGF165) is efficient for therapeutic angiogenesis in pigs. Acta. Physiol. Scand., 2002, vol. 176, No. 2, pp. 151-159, ISSN 0001-6772.

Stone, G.W. et al. Percutaneous recanalization of chronically occluded coronary arteries: A consensus document, Part I. Circulation, Oct. 2005, vol. 112, pp. 2364-2372.

Segev, A. et al. Novel approaches for the treatment of chronic total coronary occlusions. J. Interven. Cardiol. Dec. 2004, vol. 17, No. 6, pp. 411-416, ISSN 0896-4327.

Strauss, B. H. et al. Collagenase plaque digestion for facilitating guide wire crossing in chronic total occlusions. Circulation [published online], Aug. 2003, vol. 108, pp. 1259-1262, ISSN 1524-4539.

Stone, G.W. et al. Percutaneous recanalization of chronically occluded coronary arteries; Procedural techniques, devices, and results. Catheter Cardiovasc. Interv. [published online]. Sep. 2005, vol. 66, No. 2, pp. 217-236, ISSN 1522-1946.

Strauss, B.H. et al. Microvessels in chronic total occlusions; Pathways for successful guidewire crossing? J. Interven. Cardiol., Dec. 2005, vol. 18, pp. 425-436, ISSN 0896-4327.

International Search Report (ISR) and Annex thereto, established on international patent application No. PCT/CA2005/001838 (published as WO 2006/058434) on Mar. 21, 2006 (5 pages).

Written Opinion, issued by ISA (Canadian Patent Office on International Patent Application No. PCT/CA2005/001838, completed Mar. 17, 2006 (7 pages).

International Preliminary Report on Patentability (IPRP), established on international patent application No. PCT/CA2005/001838 (published as WO 2006/58434) on Jun. 5, 2007.

Carlino, Mauro et al., "CTO Recanalization by Intraocclusion Injection of Contrast: The Microchannel Technique", Catheterization and Cardiovascular Interventions, 71:20-26 (2008).

Jaffe, Ronen et al., "Natural History of Experimental Arterial Chronic Total Occlusions", Toronto, Ontario, pp. 1-33; unpublished manuscript.

Katsuragawa, Masayuki et al., "Histologic Studies in Percutaneous Transluminal Coronary Angioplasty for Chronic Total Occlusion: Comparison of Tapering and Abrupt Types of Occlusion and Short and Long Occluded Segments", JACC vol. 21, No. 3, Kyoto, Japan, Mar. 1, 1993:604-11.

Srivasta, Sanjay S. et al., "Histologic Correlates of Angiographic Chronic Total Coronary Artery Occlusions", JACC vol. 29, No. 5, Rochester, Minnesota, Apr. 1997:955-63.

Nikol, S. et al: "Local perivascular application of low amounts of a plasmid encoding for vascular endothelial growth factor(VEGF165) is efficient for therapeutic angiogenesis in pigs", Acta Physiol. Scand. vol. 176, No. 2, 2002, pp. 151-159.

Freedman S B et al: Therapeutic angiogenesis for ischemic cardiovascular disease. Journal of Molecular and Cellular Cardiology, Academic Press, GB, vol. 33, No. 3, Mar. 1, 2001, pp. 379-393, XP001057080, ISSN: 0022-2828.

Reedman S B et al: "Therapeutic angiogenesis for coronary artery disease", Annals of Internal Medicine, vol. 136, No. 1, Jan. 1, 2002, pp. 54-71, XP002531912, ISSN: 0003-4819.

Extended European search report for European Patent Application No. 05816353.6.

* cited by examiner

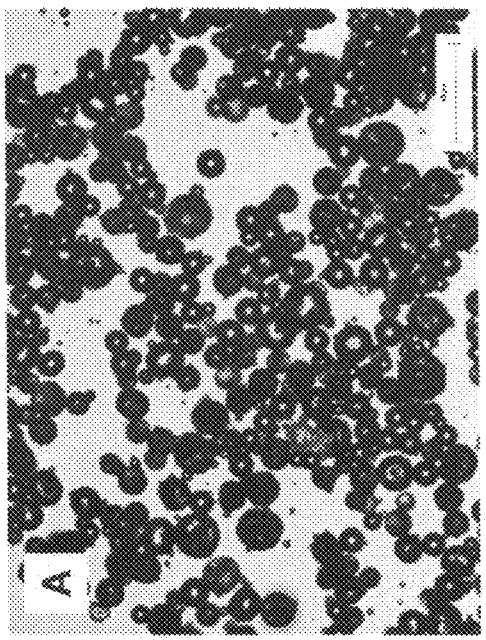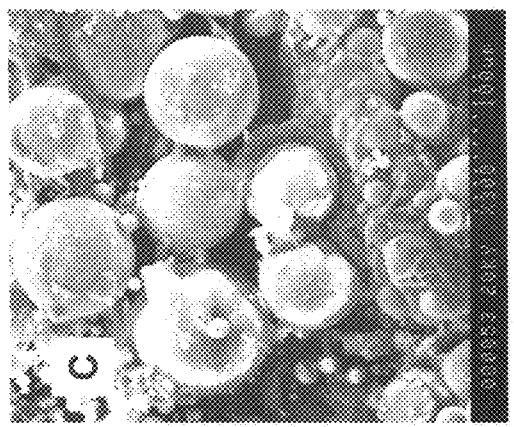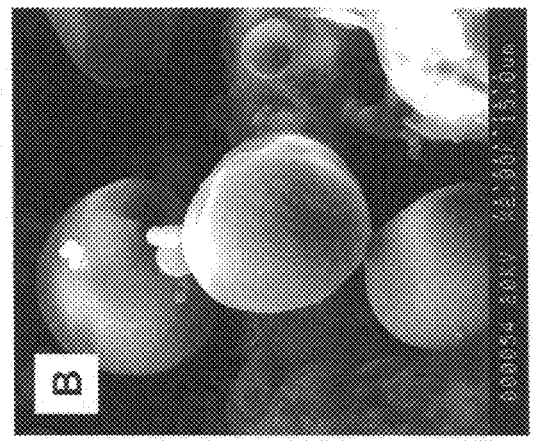
Figure 13

Figure 15: Region in red just beyond proximal part of the occlusion

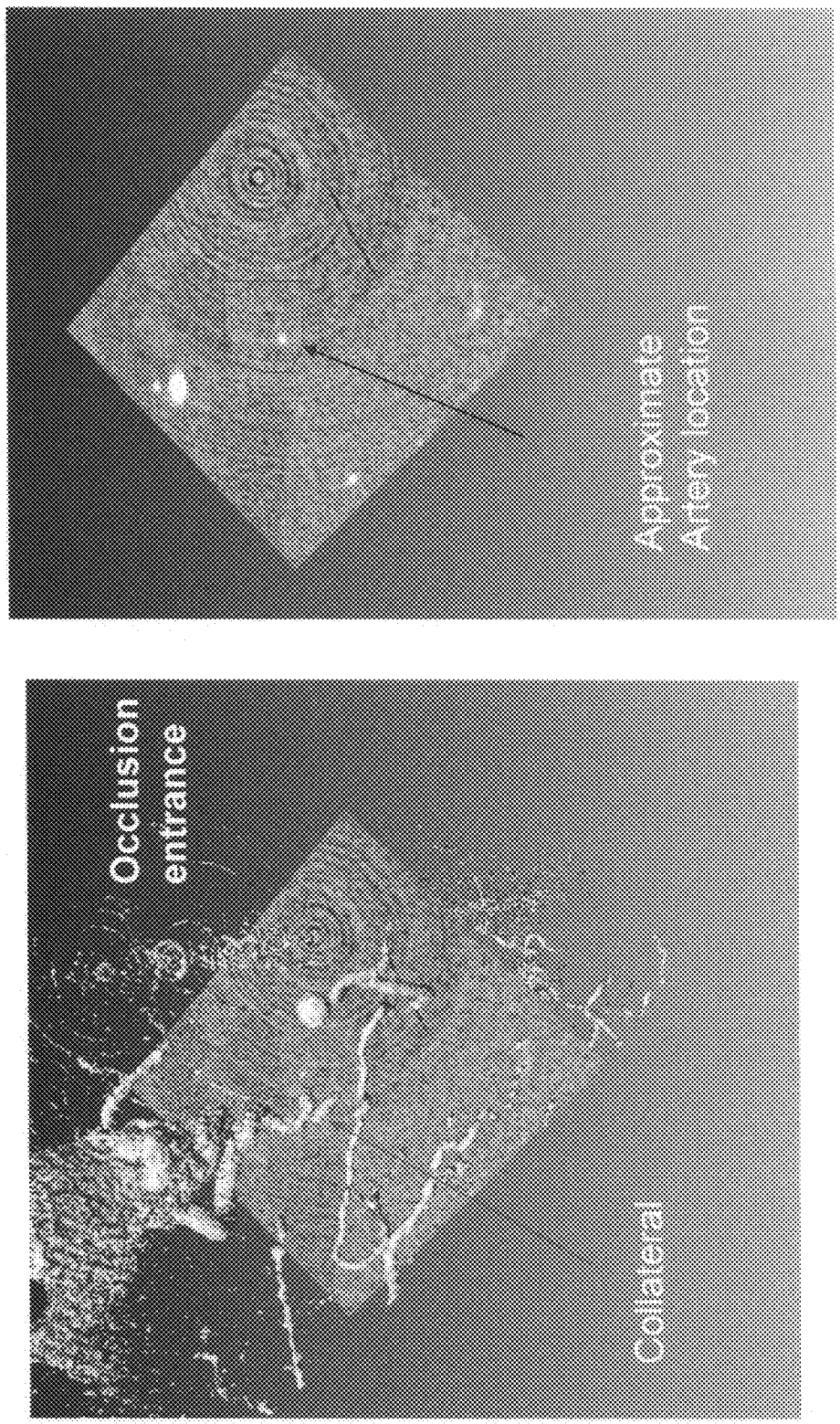
Figure 23:40671L: Absence of overlying vasculature network as compared to VEGF treated arteries

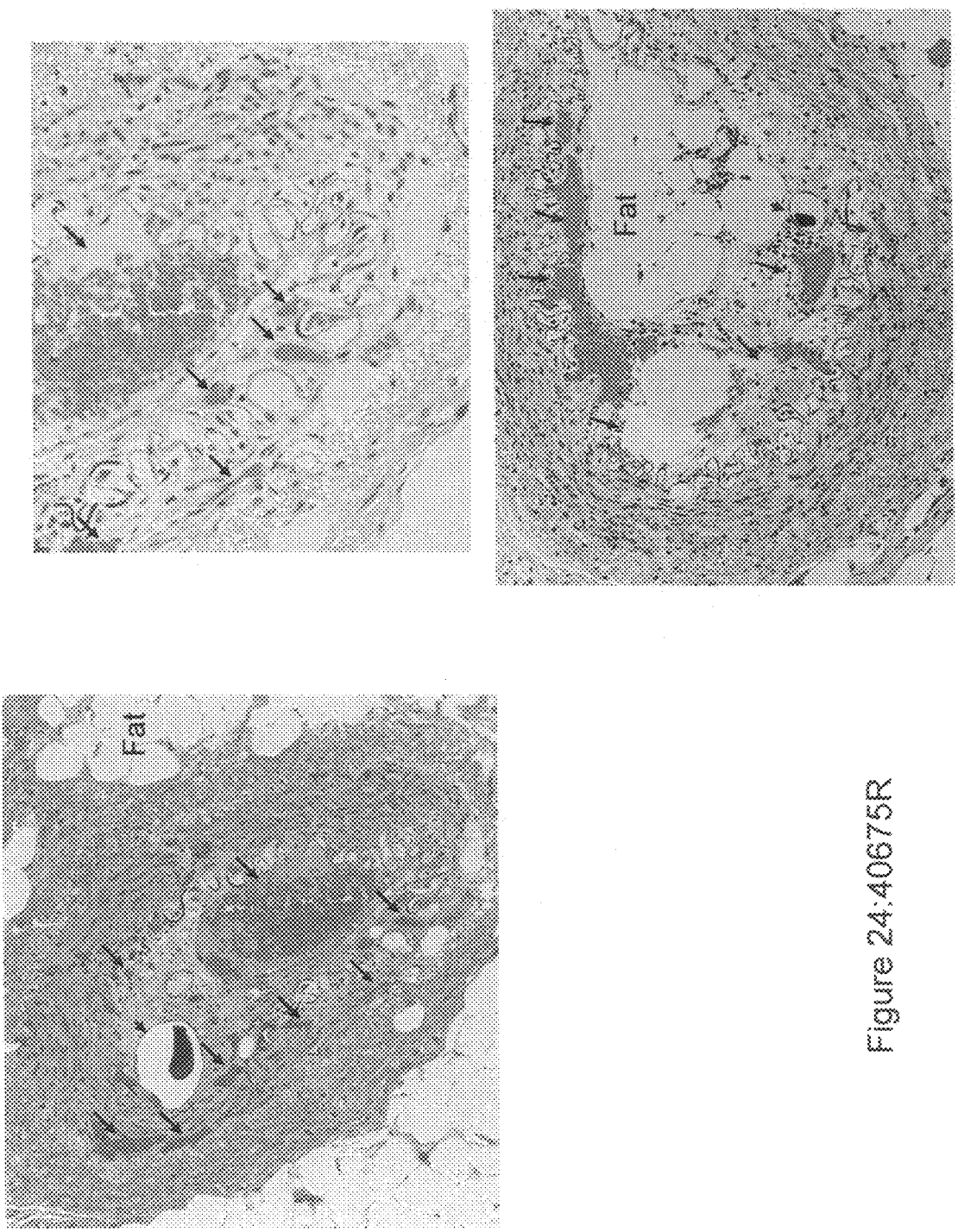
Figure 24: 40675R

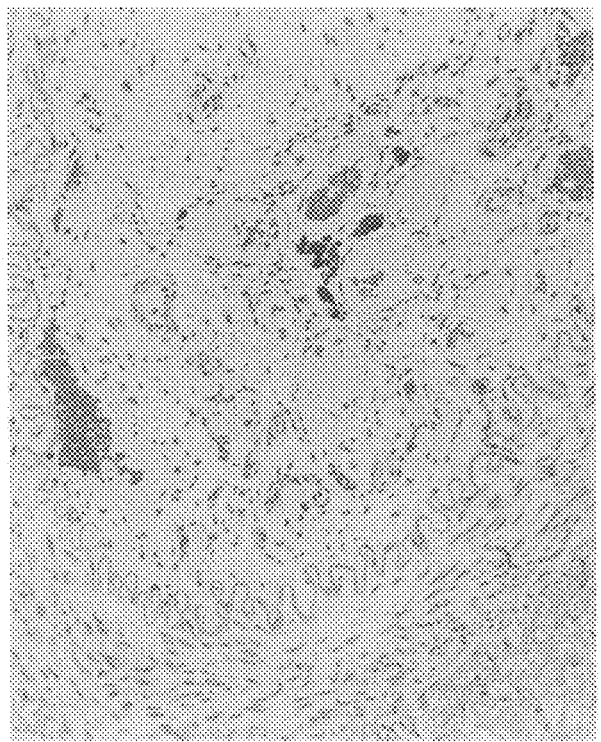
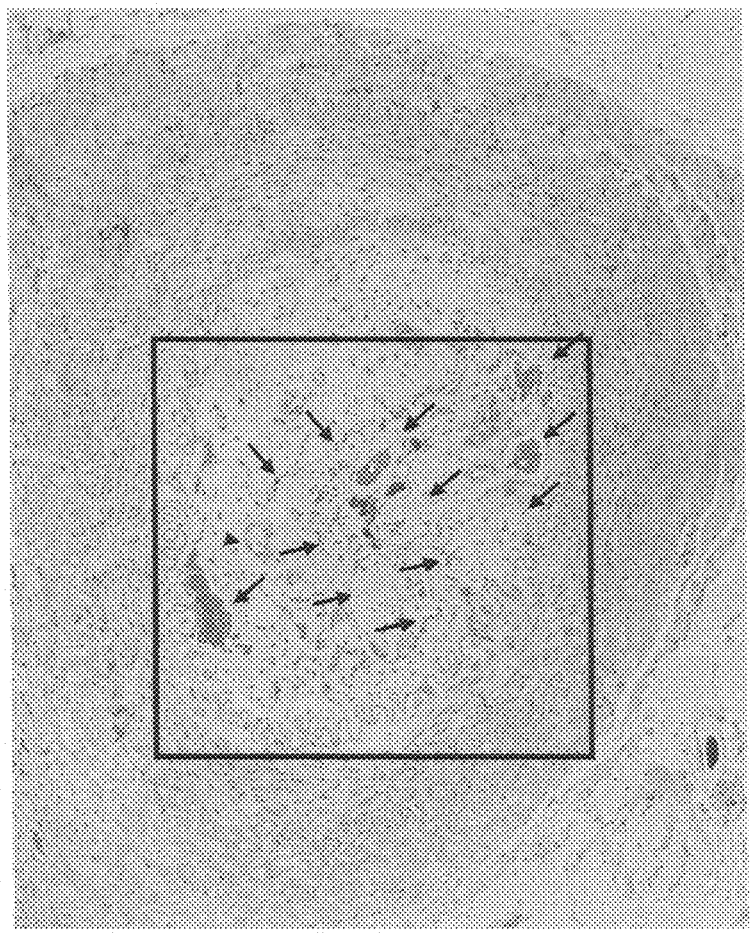
Figure 25:40676L

AUGMENTATION OF INTRALUMINAL MICROVESSEL FORMATION TO FACILITATE GUIDE WIRE CROSSING IN CHRONIC TOTAL OCCLUSIONS

RELATED APPLICATIONS

This application claims priority from U.S. Provisional Patent Application No. 60/632,267 filed Dec. 2, 2004, and this application is a continuation-in-part application of international patent application No. PCT/CA2005/001838 filed Dec. 2, 2005 and published under WO 2006/058434 on Jun. 8, 2006. The content of both of these prior applications is incorporated by reference into this application.

FIELD OF THE INVENTION

The present invention relates to percutaneous interventions of occluded vessels, e.g., arteries by augmenting intraluminal microvessel formation by local pro-angiogenic therapies.

BACKGROUND OF THE INVENTION

Coronary artery disease remains the leading cause of mortality in the western world. Chronic total occlusions (CTO), defined as occlusions of more than a month old, are very common in patients undergoing diagnostic coronary artery catheterization with up to 20% of patients reported to have one or more CTO (1). This includes a large number of patients that have not actually had a myocardial infarction. Successful revascularization of CTO significantly improves angina in symptomatic patients (2, 3) and more recent data demonstrate improvement in left ventricular function (4-7), and even in reduction of mortality (8-10). Currently there are two possible therapeutic strategies for CTO revascularization: coronary artery bypass graft surgery (CABG) or percutaneous coronary interventions (PCI) (angioplasty or stenting). Successful angioplasty requires that the operator place a small (360 µm diameter) guide-wire through the tissue obstructing the lumen in a CTO in order to reach the distal arterial lumen. The technical difficulty of performing PCI in CTO, primarily because of inability to cross CTO with a guide wire, is reflected in the low rates of PCI for CTO (accounts for <8% of all PCI), despite the benefits of a positive outcome (11). Since PCI have severe limitations in this patient subset, clinicians frequently decide to refer these patients for CABG or persist with (often ineffective) medical therapy. The presence of one or more CTO of vessels supplying viable myocardium remains one of the most common reasons for referral for CABG rather than attempting PCI (12).

The definition of a CTO is based on an angiographic appearance of complete absence of contrast reagent in a segment of an epicardial coronary artery. The distal artery beyond the CTO may not be visible or may be perfused by anterograde collaterals that are outside of the vessel lumen (termed "bridging collaterals") or by retrograde collaterals that originate from adjacent coronary vessels. Procedural success rates in stenotic (but non-occluded) coronary artery lesions are in excess of 95%. However, procedural success rates for CTO are only in the 60 to 70% range (3, 13, 14), with only modest improvement over the 50-60% success rates in the 1980's (23, 24), despite some improvements in angioplasty technology (25, 26). This current success rate for CTO is probably an overestimation in the sense that the majority of CTO are probably never even attempted due to expected failure.

Inability to cross the CTO with a guide-wire is responsible for upwards of 75% of PCI failures (14, 15). In a minority of cases, the balloon or stent cannot cross the lesion despite successful guide-wire crossing. Despite its common occurrence, there is surprisingly little information about the pathophysiology of CTO, and why some CTO can be crossed while others are unsuccessful.

The initial acute event leading to the development of a CTO is a ruptured atherosclerotic plaque with bidirectional thrombus formation. The thrombus and lipid-rich cholesterol esters are gradually replaced over time by the formation of collagen and calcium deposits (16, 17). This fibrous tissue is particularly dense at the proximal and distal ends of the lesion, which typically are the most resistant areas of the CTO for guide-wire crossing. Proteoglycans are also important components of the CTO within the first year (16). In later stages, the lesion becomes more calcified (16, 17). Despite the angiographic appearance of a CTO, microvessels are quite common in CTO (>75%), regardless of occlusion duration (FIG. 1) (16).

There are three types of microvessel formation in arteries with advanced atherosclerotic lesions. The first pattern occurs in the vasa vasorum, which are the fine network of microvessels in the adventitia and outer media. These vessels proliferate in atherosclerosis and in response to vascular injury such as angioplasty and stenting (18-20). Hypoxia in the outer levels of the vessel wall appears to act as an important stimulus (36). Occasionally in CTO, these adventitial blood vessels are well developed and can be recognized as "bridging collaterals". Second, neovascularization can develop within occlusive intimal plaques, predominantly in response to chronic inflammation (21). Plaque neovascularization has been associated with progression of experimental atheromas in various animal models (22-25). The localization of plaque vessels in so-called "hot spots" in the shoulders of atheromas may predispose these plaques to rupture and acute coronary events (26, 27). The third type is the pattern of microvessel formation (known as "recanalization") that occurs as part of the organization phase in CTO in which thrombus is replaced by fibrous tissue. These microvessels generally range in size from 100-200 µm but can be as large as 500 µm (21). In contrast to the vasa vasorum which run in radial directions, these intimal microvessels run within and parallel to the thrombosed parent vessel (28).

Knowledge of thrombus organization comes largely from the study of veins. This process resembles the pattern of wound healing (29). Initially, the freshly-formed thrombus contains platelets and erythrocytes within a fibrin mesh, which is followed by invasion of acute inflammatory cells (44). Neutrophils predominate at first but are later replaced with mononuclear cells. (30, 31). Endothelial cells also invade the fibrin lattice and form tube-like structures and microvessels within the organizing thrombi (29, 32).

Relatively little is known about the process of microvessel formation in arterial thrombi. It cannot be assumed that the processes are identical in veins and arteries. Arterial thrombi recanalize less frequently and to a lesser extent than venous thrombi (33). The behavior of venous cells can differ substantially from their arterial counterparts (34, 35). Microvessels have been reported in 2-week-old mural thrombi in porcine aortas, which were attributed to mononuclear blood cells originating within the thrombus, with no apparent contribution from cells native to the vessel wall (36) or from invasion of vasa vasorum from the vessel wall (37, 387). Inflammation may also play a role since high concentrations of macrophages have been detected in regions of recanalization in spontaneous human thrombi and in experimental animal arterial thrombi (31, 39). The local ECM environment is probably an additional important modifier, with specific matrix components exerting either a pro-angiogenic (hyaluronan (40, 41), fibronectin (42, 43), perlecan (44-46), versican (47)), or anti-angiogenic (type I collagen (40, 48) decorin (49, 50)) effects.

We have observed the presence of a variable number of microvessels in CTO. These preliminary observations suggest the possibility that these microvessels assist in successful CTO guide-wire crossings (see below). Microvessels have also been observed in a limited number of human coronary CTO studies (16), which has led us to the concept that intraluminal vascularization, and its effects on structural and mechanical properties of lesion, may substantially facilitate CTO guide-wire crossing rates. This can be studied using imaging techniques including magnetic resonance imaging (MRI) and 3D micro computed tomography (micro CT).

SUMMARY OF THE INVENTION

In accordance with the present invention, an approach to improve the current probability of a successful guidewire crossing of an occlusion in a mammalian vessel is described. Usually, a vessel is prepared so as to be capable of crossing of an occlusion situated therein by a guidewire of an intraluminal device, e.g. the guidewire of a balloon angioplasty catheter. Typically, the occlusion is a chronic total occlusion and vessel is a human artery, frequently located in the heart.

In accordance with the invention, the occlusion is prepared for crossing by inducing angiogenesis therein.

According to one aspect, the invention is a method of crossing a chronic total occlusion of a human. The method includes (i) inducing angiogenesis in the occlusion; and (ii) crossing the occlusion.

Often, the invention involves (a) delivering an angiogenic agent to the occlusion site; (b) waiting a period of time sufficient to increase susceptibility of the occlusion to crossing through angiogenesis; and (c) crossing the occlusion. The agent can be delivered systemically. The agent is more typically delivered percutaneously directly to the site of the occlusion.

In addition to inducing angiogenesis in an occlusion, other steps may be incorporated into the invention in preparing an occlusion for crossing, as exemplified throughout this specification.

A potential advantage of the invention is an effective increase in intraluminal microvessel formation in a way that facilitates guide wire crossing and improves procedural success rates, without causing adverse effects to the vessel wall.

The present invention is directed to a method of treating chronically occluded animals tubes such as fallopian tubes, ureters, and bile ducts.

In a specific embodiment, the invention is a method for treating chronically occluded animal tubes and cavities. The first step in the method is administering a therapeutic effective amount of a pro-angiogenic substance(s) to an occluding atherosclerotic plaque. The substance(s) is delivered directly to a location adjacent the plaque to be brought into contact therewith, or in some embodiments, the substance(s) is delivered systemically, ultimately to be brought to the plaque. A combination of delivery methods is contemplated. There follows a pre-angioplasty waiting period prior to crossing the plaque with an angioplasty guide wire. This waiting period (1 day to 8 weeks, more likely between 2 days and 7 weeks, or 3 days and 6 weeks, or 4 days and 5 weeks, or 5 days and 4 weeks, or between about 1 and 3 weeks, often about 2 weeks) is required for the new microvessel formation. Following the waiting period, the occlusive plaque is crossed with an angioplasty guide wire.

In another aspect, the invention is a method of preparing a vessel for crossing of an occlusion situated therein that includes delivering an angiogenic agent to the occlusion site. Delivering the angiogenic agent can include inserting a delivery device containing the agent directly into the vessel for deposition therein. In a particular aspect, the device includes a catheter, and delivering the agent to the occlusion site includes conveying the agent the vessel through the catheter. The distal end of the catheter can be brought within 10 cm of the occlusion prior to conveying the agent to the site through the catheter. The distal end, i.e., the delivery end of the catheter from which the agent emerges into the vessel is often brought into closer proximity of the target site, within 5 cm, or within 4 cm, or within 3 cm or even within 2 cm of the site. Delivering the agent to the occlusion site often includes bringing the agent into direct contact with the occlusion.

Delivering the angiogenic agent can include lodging a device within the vessel in the proximity of the occlusion, the device being loaded with the agent. The agent is released from the device over an extended period of time, say up to about two hours, or between 20 minutes and 90 minutes or between 40 minutes and 60 minutes.

A second device can be introduced into the vessel to retain the agent in direct contact with the occlusion for a period of time. Such period of time is preferably a predetermined period sufficient to induce angionenesis in the occlusion. Where appropriate, of course, angiogenesis within the occlusion is monitored, either directly or indirectly. Such period of time is likely to be between one day and ten weeks, or between two and fifty days, or between three and forty days, or between seven and thirty days, or between fourteen and twenty-eight days.

Occluded vasculature of prime relevance to the invention is the human arterial system generally, particularly arteries of the heart, a peripheral artery, a femoral artery, a popliteal artery, a subclavian artery, or a brachial artery.

The can include monitoring the occlusion for the development of microvessels therein subsequent to delivery of an angiogenic agent. Such monitoring could involve imaging the occlusion using magnetic resonance.

Angiogenic agents of the invention include angiogenic or pro-angiogenic growth factors and/or cytokines or combinations of growth factors and/or cytokines of the invention include vascular endothelial growth factor; angiopoietin 1, 2; PDGF, FGF-2, TGF-beta, hepatocyte growth factor, TNF-alpha, endothelium-derived nitric oxide or nitric oxide donors, growth factor receptors (VEGFR-1, VEGFR-2, PDGFR, tie2), and hypoxia inducible factor (HIF) 1-alpha, including combinations thereof.

An angiogenic agent of the invention can be a stem cell, possibly one that originates from an embryo or bone marrow or circulating blood of adults or endothelial progenitor cells (EPC), and possibly one that has increased angiogenic potential by genetic manipulation of the EPC to overexpress angiogenic growth factors such as eNOS or VEGF.

The invention can further include the delivery of a growth factor such as granulocyte-macrophage colony-stimulating factor, erythropoietin and/or statin so as to mobilize a pro-angiogenic factor into the circulation.

Also, the invention can include inducing overexpression of extracellular matrix components in the occlusion that are pro-angiogenic such as hyaluronan, fibronectin, perlecan, and/or versican.

An again, the invention can include delivering matrix metalloproteinases such as collagenase to the occlusion to enhance angiogenesis in the occlusion.

The invention can also include delivering macrophage colony stimulating factor (M-CSF) to the occlusion.

In another aspect, the invention includes delivering a substance that causes activation of macrophages or chemotaxis of macrophages to the chronic total occlusion to the site of the occlusion.

In another aspect the invention includes a method of inducing and/or promoting angiogenesis in an atherosclerotic plaque of a mammal, the method comprising percutaneously delivering an angiogenic agent through a tube directly to the plaque site. The tube is typically a catheter inserted into the blood vessel containing the plaque.

According to another aspect, the invention is a method of crossing a chronic total occlusion having the following steps: (1) percutaneously delivering a composition comprising an angiogenic agent to the occlusion site; (2) waiting a period of time sufficient to increase susceptibility of the occlusion to crossing through angiogenesis; and (3) crossing the occlusion. The period of time is usually between about 24 hours and three months, at times at least five days, or as otherwise described herein.

One embodiment of the invention includes a method of treating an occluded artery that involves (I) advancing a drug delivery device through the artery to the occlusion, the device containing a composition containing an angiogenic agent; (II) releasing the composition from device to bring the composition and occlusion into contact with each other; (III) withdrawing the drug delivery device; (IV) waiting a period of time sufficient to permit sufficient angiogenesis to occur in the occlusion to permit crossing of the occlusion by a guide wire; and (V) crossing the occlusion with a said guide wire.

The invention can be embodied in a pharmaceutical composition for inducing angiogenesis in an occlusion of an artery, the composition comprising an angiogenic agent in a form suitable for percutaneous delivery to a chronic total occlusion located in the artery of a human.

In another embodiment, the invention is a kit comprising a pharmaceutical composition for inducing angiogenesis in an occlusion of an artery. The kit includes a first package containing an angiogenic agent and a second package containing a diluent. The contents of the packages are mixed to produce an angiogenic agent in a form suitable for immediate delivery through a catheter to a chronic total occlusion located in the artery of a human.

The kit can further include a device for delivery of the composition to the occlusion and/or instructions for use of the components of the kit according to the methods of the invention.

The invention includes use of an angiogenic agent in the induction of angiogenesis in an occlusion of a vessel of a human, optionally a chronic total occlusion of an artery located in the heart of the human.

The invention includes use of an angiogenic agent in the manufacture of a medicament for inducing angiogenesis in an occlusion of a human vessel, optionally a chronic total occlusion of an artery located in the heart of the human.

BRIEF DESCRIPTION OF THE DRAWINGS

Particular aspects of the invention have been chosen for purposes of illustration and description, but are not intended in any way to restrict the scope of the present invention. Preferred embodiments of the invention are included in the following description including the drawings wherein:

FIG. 13(a) is a light micrograph (20× magnification) and FIG. 13(b) (×2000 magnification) and 13(c) (×300 magnification) scanning electron micrographs, demonstrate empty PLGA microspheres that were used to deliver VEGF and BSA to the CTO. The microspheres in shown in FIG. 13(b) are approximately 15 microns diameter.

FIG. 15(a) shows the CTO prior to treatment and FIG. 15(b) shows the CTO three weeks after treatment. The proximal border of the occlusion is indicated by the arrow.

FIG. 19(a) used high sensitivity detection to detect fine vasculature surrounding the artery. The proximal border of the occlusion is marked by the arrow. At that site, a cross-section micro-CT image is also shown with the stump of the occluded artery in the middle of the cross-section. Collateral vessels are shown beyond the occlusion site and are outside the plane of the occluded vessel. FIG. 19(b) shows the same site but using much lower sensitivity threshold parameters. In addition to the main vasculature shown in yellow, there are a large number of finer, smaller microvessels appearing as brown color. These microvessels extend into the occlusion beyond the proximal border and are both in-plane of the occluded vessel and out of plane (ie extravascular small collateral vessels).

In FIG. 20(a), the main vessel obtained by MIP image and smaller collateral vessels appear as yellow structures. In the cross-section, the enhancement of the vessel in the periphery is indicated by an arrow. In FIG. 20(b), the MIP overlay has been removed and the main vessel at the proximal border of the occlusion is indicated by the arrowhead.

FIGS. 21(a) and 21(b) are micro-CT images similar to FIGS. 19(a) and 19(b) for a second VEGF rabbit.

FIG. 22(a) is a MIP image at higher sensitivity threshold resolution and FIG. 22(b) is a MIP image at lower sensitivity threshold resolution. Some well-formed collaterals appear in the lower sensitivity threshold image (blue color) but there are essentially none of the smaller, very fine vessels seen in FIGS. 19(b) and 22(b) beyond the proximal border of the occlusion.

FIGS. 23(a) and 23(b) are micro-CT cross-sections of a control (saline-treated) occlusion at the proximal site of the occlusion, similar to FIG. 20. In FIG. 23(a), the MIP overlay shows the stump of the main vessel at the proximal border of the occlusion as well as a large collateral (arrows). In FIG. 23(b), the MIP overlay has been removed and the stump of the main vessel appears as the circle within the red region. In these cross-section images at this level, there is no enhancement at the periphery of the artery as seen in FIG. 20, indicating absence of the small, fine vessels seen in FIG. 20.

FIGS. 24(a), 24(b) and (c) are light micrographs of femoral artery occlusions obtained at 3 weeks after VEGF therapy, stained with hematoxylin and eosin. FIG. 24(b) (×40 objective) is an enlargement of black area defined in FIG. 24(a). FIGS. 24(a) and 24(b) were both obtained with ×20 objective and were located at the proximal ⅓ of the total occlusion.

FIGS. 25(a) and (b) are light micrographs of a femoral artery occlusion obtained at 3 weeks after VEGF therapy in a second rabbit, stained with hematoxylin and eosin. FIG. 25(b) (×40 objective) is an enlargement of the block area defined in FIG. 25(a). FIG. 25 (a) was obtained with ×20 objective and was located at the proximal ⅓ of the total occlusion.

DETAILED DESCRIPTION OF THE INVENTION

Angiogenesis and Angiogenic Growth Factors

Figure 1A:
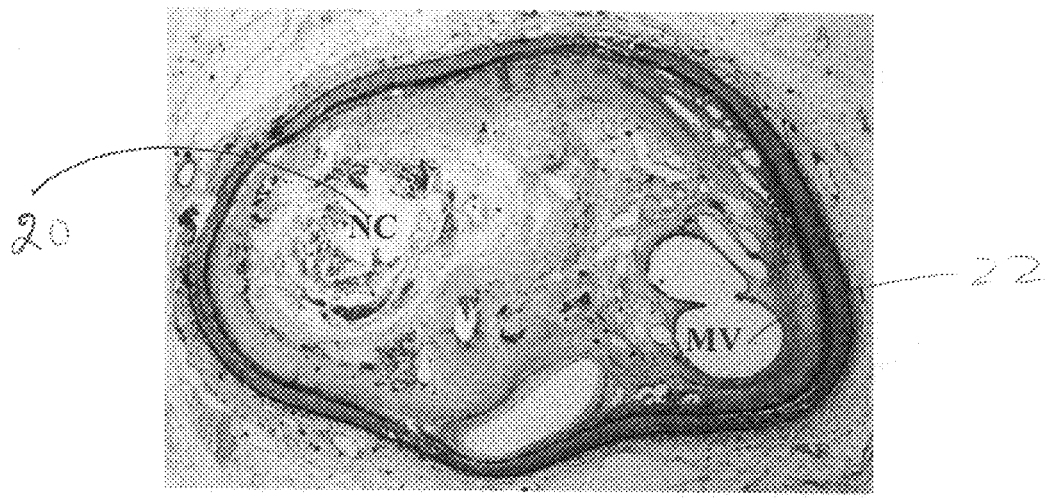
FIG. 1 shows human coronary artery chronic total occlusion: (a) Movat Stain; and (b) Factor VIII stained (for endothelial cells).

Angiogenesis is a process that results in the formation of new blood vessels from preexisting vasculature (51-53). This process is initiated by vasodilation and increased permeability of the existing microvessels. This is followed by coordinated proteolysis, resulting in the destabilization of the vessel wall, endothelial cell migration and proliferation and subsequent tube formation (54, 55). Maturation of these primitive endothelial tubes requires recruitment of the supporting cells, pericytes or SMC and deposition of ECM (56). Multiple growth factors are involved in various aspects of angiogenesis, including vascular endothelial growth factor (VEGF), platelet derived growth factor (PDGF) and its receptor PDGFR-β (57, 58), angiopoietin-1 and tie2 receptor (55, 56, 59-61), fibroblast growth factor-2 (FGF-2) (62), TGFβ (63), and endothelium-derived nitric oxide (64, 65). VEGF and its receptor, VEGFR2, are specifically germane to the invention described herein.

VEGF is the major pro-angiogenic growth factor that stimulates endothelial cell differentiation, tube formation, migration and proliferation, increases endothelial permeability and acts as an endothelial survival factor (66, 67). VEGF is up-regulated during tissue hypoxia (68-71), and promotes sprouting angiogenesis in response to hypoxia (69, 70, 72), a response that involves induction of the transcriptional regulator of VEGF expression, hypoxia-inducible factor-1 alpha (HIF-1α) (72, 73). VEGF mediates its biologic effects through specific high affinity tyrosine kinase receptors flk-1/KDR (VEGFR2) present on endothelial cells (74, 75). In a rat venous thrombosis model, VEGF concentration in the thrombus doubled from day 1 to day 7. VEGF antigen was localized to monocytes, endothelial cells and spindle-shaped cells within a 7-day-old thrombus (75). Injection of VEGF protein into venous thrombi in the rat model increased thrombus recanalization (two-fold) compared to controls (76).

Microvessel Imaging Techniques

The imaging of CTO has been traditionally restricted to contrast angiography, which is limited both by detector resolution of about 250 um and an inadequate contrast concentration required to opacify the x-ray signal in smaller coronary vessels. Contrast angiography also provides no information about the composition of the total occlusion. Since the vessel must be opacified by iodinated contrast to be visible on x-ray, there is also, no information in regard to the geometry of the occlusion. The presence of a "blush" of contrast within the CTO as seen on angiography may indicate the presence of microvessels, but because the image created by x-ray is a projection image through the entire body, the exact location, size, and number of these microvessels cannot be determined. Various vascular imaging techniques are particularly useful in the study of CTO in our in vivo model.

Magnetic resonance imaging (MRI) provides high contrast sensitivity but relatively low resolution in vivo non-invasively. Working at high field (3T) with small local imaging coils in the proposed rabbit CTO model, we can achieve reasonable spatial resolution down to 100-200 um (um=micrometer (i.e., μm) throughout this application) in plane and about 1 mm through-plane. MRI offers multiple advantages for CTO imaging. MRI offers soft tissue discrimination for determining the spatial composition of atherosclerotic plaque components such as lipid, thrombus, fibrous tissue and calcium based on signal intensities in T1-, T2-, and proton density (PD) weighted images (77, 78). The use of specific MR contrast agents (Gd-DTPA, Clariscan) permits calculations of relative extracellular volume and blood volume within regions of the CTO. Gd-DTPA leaks into the extracellular space from the vasculature and MR measures of its rate of entry and distribution (79) in the occlusion can be related to microvascular density and permeability, reflecting the environment of new blood vessel formation. A second contrast agent, Clariscan (also referred to as NC100150-Injection or feruglose), remains inside vessels, and hence can be used to estimate relative blood volume in the CTO (80, 81). Measures of distribution volume and blood volume with Gd-DTPA and Clariscan respectively are derived from signal intensity in T1-weighted images since T1 is linearly related to concentration of the agent in tissue assuming rapid exchange of water among different pools. As such, these measures provide information about the agent accumulating in spaces below the imaging resolution.

3D micro CT (Micro CT) is a relatively new high-resolution imaging technique that provides detailed rendering of complex microscopic vascular structures (20 um resolution), and produces precise 3D images of the arterial microvasculature (82). Micro CT is performed ex vivo on excised vessels that have been perfused with Microfil (Flow Tech Inc, Carver, Mass.), a low-viscosity, lead chromate-doped silicon polymer compound. This agent fills the vascular space down to arteriolar level and does not reach the venous system. The angiogenic response is quantified by assessing the density and distribution of microvessels in the CTO, as recently reported by our group and others (20, 83, 84).

Figure 1B:
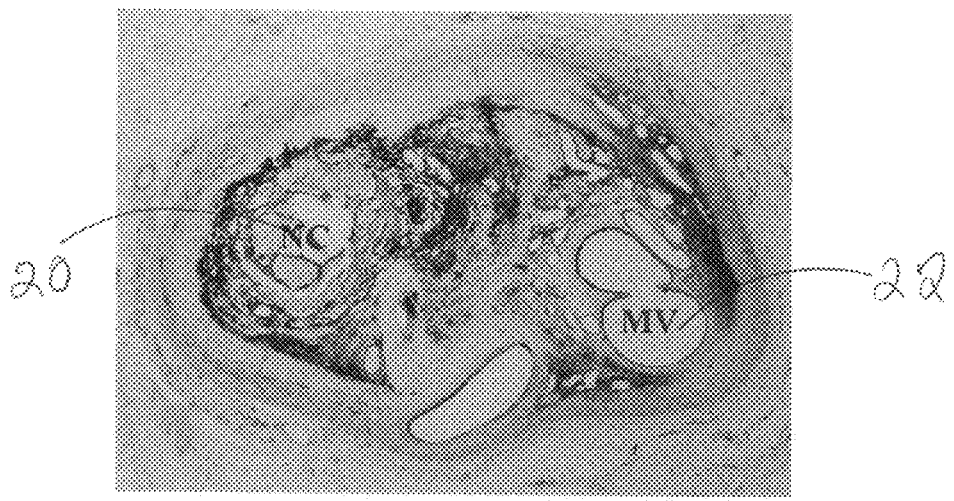
Figure 2A:
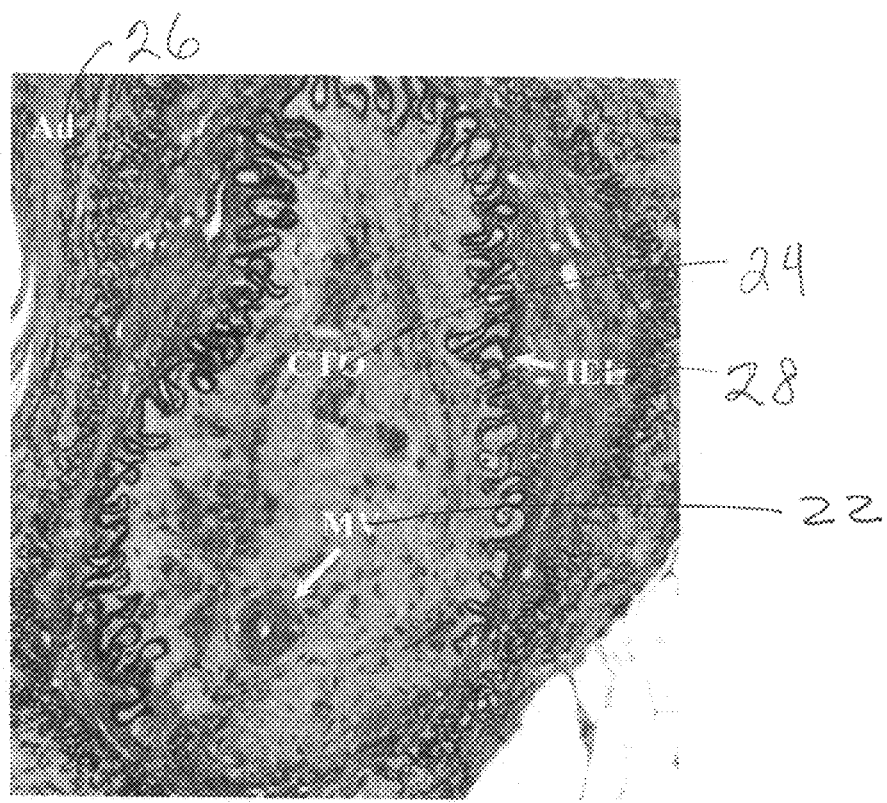
FIG. 2 shows: (a) Movat stain; and (b) Hemotoxyline and Eosin (H&E) stain of 16-week old animal model CTO that failed guide-wire crossing.
Figure 2B:
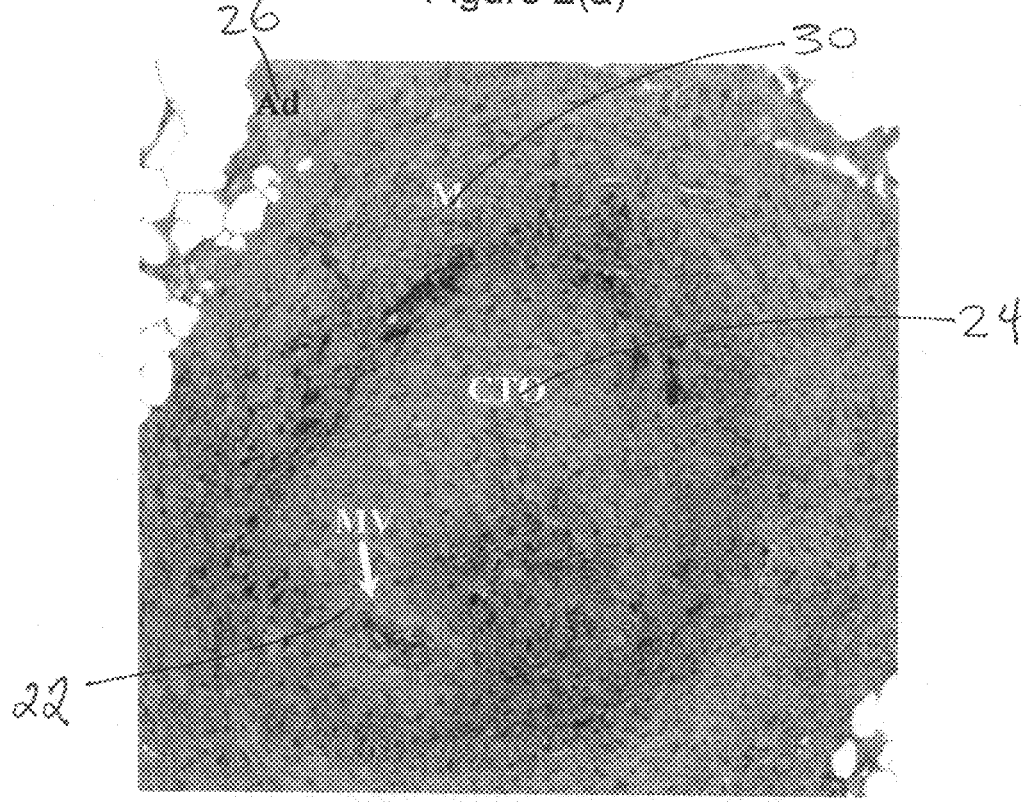

Turning to the illustrations, FIGS. 1(a) and 1(b) show a human coronary artery chronic total occlusion. FIG. 1(a) is a Movat Stain while FIG. 1(b) is Factor VIII stained, for endothelial cells. Collagens are the major structural components of the extracellular matrix, while proteoglycans are common in CTO less than a year old. Intimal plaque neovascular channels are common, occurring in greater than 75% of CTO. One can see the necrotic core 20 and microvessels 22. FIG. 1 shows the presence of a variable number of microvessels in CTO as well as the preponderance of collagen in the extracellular matrix. We have developed a CTO model in rabbit femoral arteries (85, 86), which shares many similarities with human coronary, including mature fibrous tissue, small intraluminal vascular channels, occasional extracellular lipid deposits, macrophages and lymphocytes, as shown in FIGS. 2(a) to 3(b). Movat stained sections of FIGS. 2(a) and (b) show the predominance of dense collagen in the extracellular matrix, which are light brown—yellowish staining in Movat stain. There are only a few small microvessels present, indicated by the arrows. In the figures, CTOs are generally indicated by reference numeral 24, and the adventitia 26, internal elastic lamina 28, and media 30 are also visible. In contrast to FIG. 2, there are abundant microchannels in the CTO of FIG. 3(a), indicated by the arrows. This CTO was only used for pathology and no guide-wire attempt was made. In FIG. 3(b), multiple microvessels, indicated by arrows, both thin walled channels and thicker walled arterioles can be seen. Blue staining in region of microvessels, consistent with proteoglycans, was observed. A guide wire successfully crossed the CTO in FIG. 3(b), indicated by the number (32). FIG. 3(c) is another example of microvessel-rich CTO. FIG. 3(c) shows a Movat stain of a 13-week-old CTO with extensive microchannels, indicated by the arrows. Again, blue staining adjacent to microvessels, due to presence of proteoglycan-rich tissue, could be seen. No guide-wire crossing was attempted in FIG. 3(c).

We have recently reported a novel approach to improve guide wire crossing by altering the ECM composition of the CTO with local delivery of a bacterial collagenase formulation. Compared to placebo, this strategy significantly increased guide-wire crossing success rate from 29% to 62% (85). Initial results were confirmed with a human-grade purified bacterial collagenase (86).

The present invention can also complement collagenase therapy or treat cases of collagenase failure. An unexpected yet important observation in our CTO model was the marked variability in intra-plaque microvessels. Histologic evaluation of experimental CTO lesions has suggested a correlation between the extent of microvessel formation and successful CTO guide-wire crossing. FIGS. 2(a) and 2(b) show a CTO with few microvessels that failed guide-wire crossing, while FIG. 3(b) shows an example of a CTO with abundant microvessels that was successfully crossed with guide-wire 32. The presence of microvessels appears to correlate angiographically with a more tapering type occlusion (87), which has been identified as a favorable feature for successful guide-wire crossing.

Figure 3A:
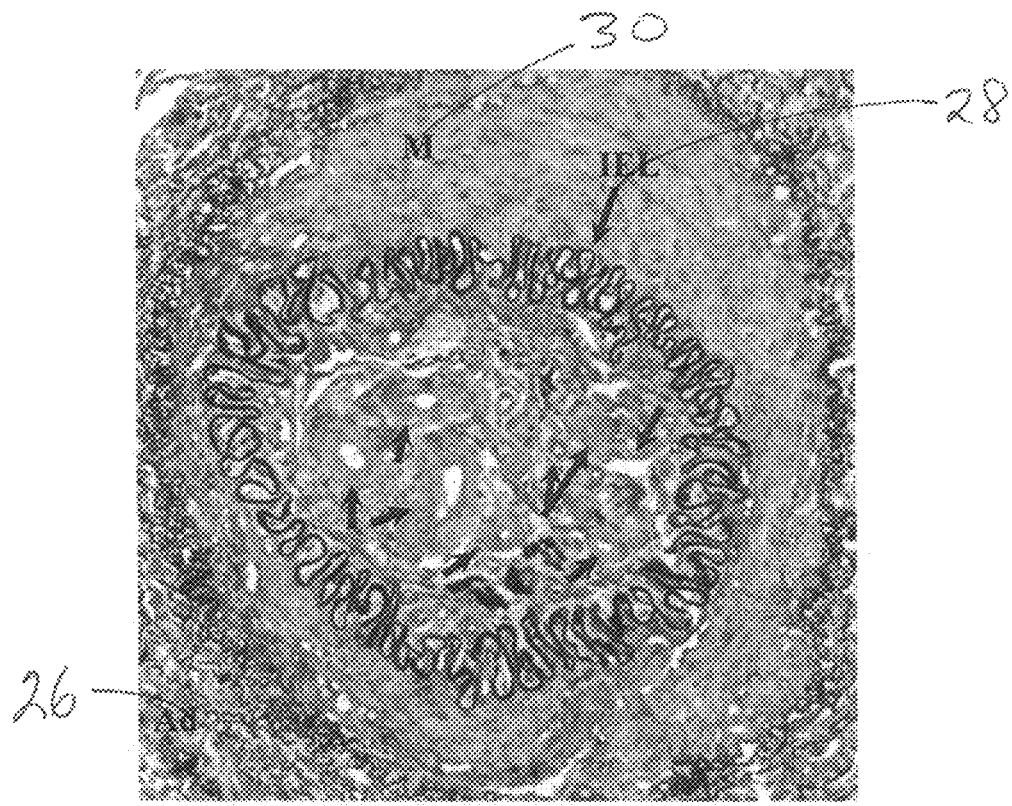
FIG. 3 shows Movat stains of: (a) a 12-week-old CTO with abundant microchannels; (b) an 18-week-old CTO successfully crossed with guide wire; and (c) Movat stain of a 13-week-old CTO with extensive microchannels.
Figure 3B:
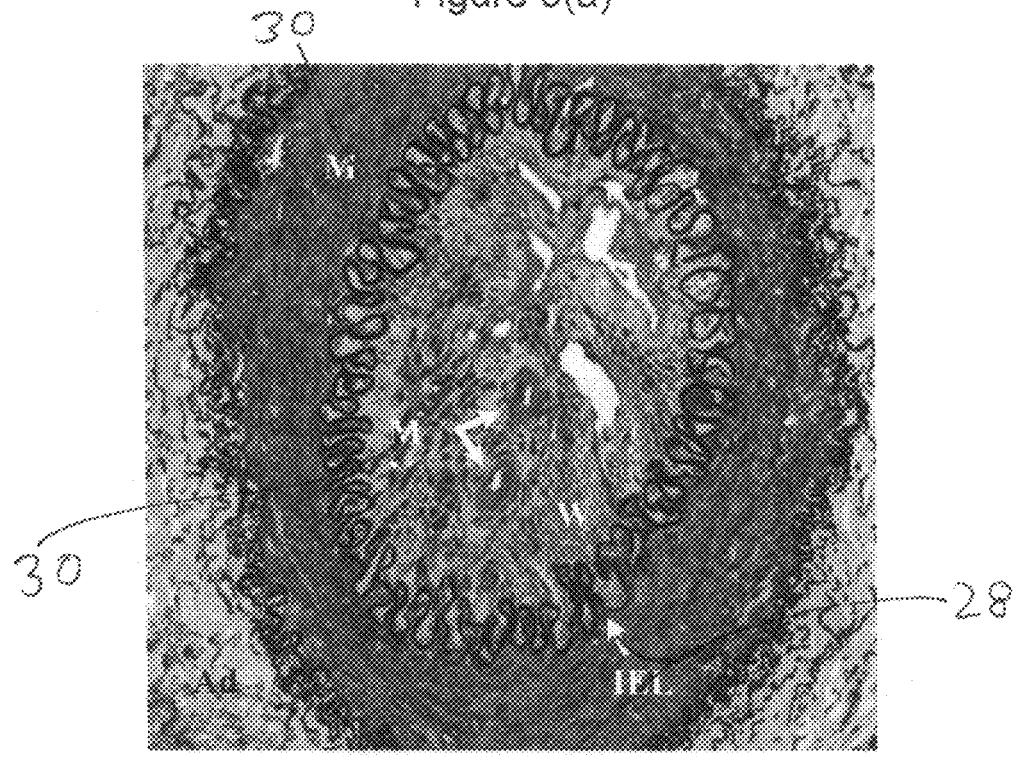
Figure 3C:
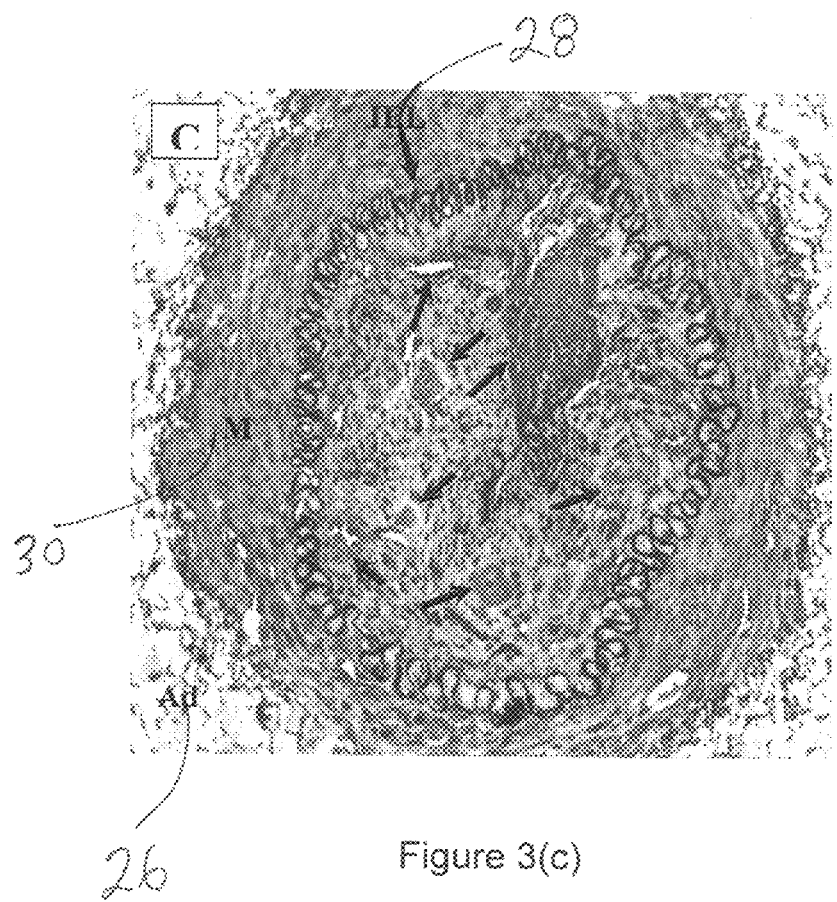

In considering whether the presence of ECM components might contribute to differences in microvessel formation, Movat slides were reviewed and it appeared as though there was increased staining for proteoglycan-rich tissue in vascular regions (FIGS. 3(a) to (c)) compared to dense collagen deposition with paucity of proteoglycans in avascular regions of CTO (FIGS. 2 (a), (b).

Figure 4A:
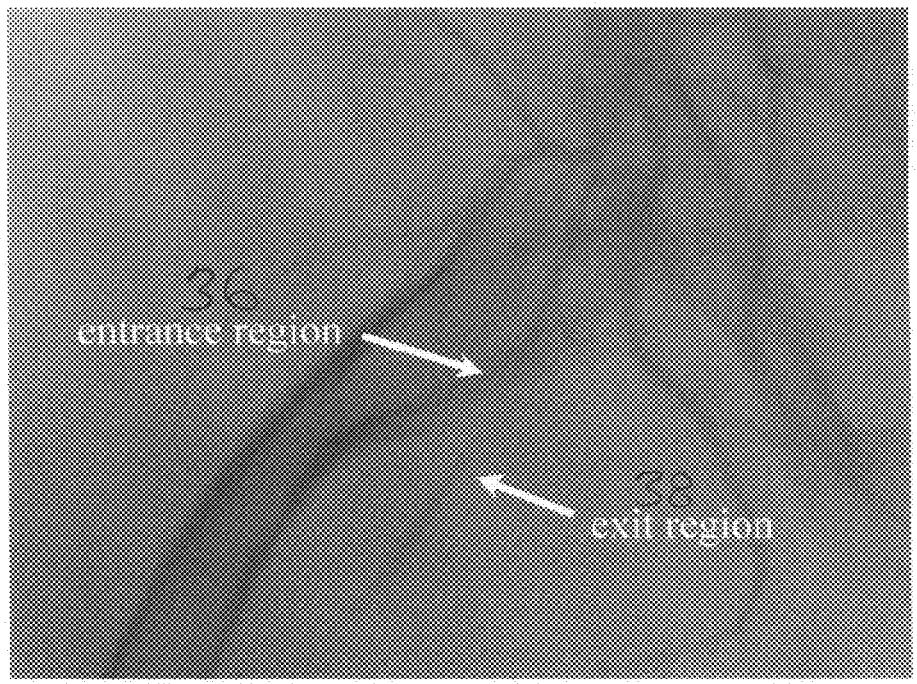
FIG. 4 shows contrast x-ray angiogram showing femoral artery CTO in rabbit at: (a) 6 weeks; and (b) 12 weeks.
Figure 5A:
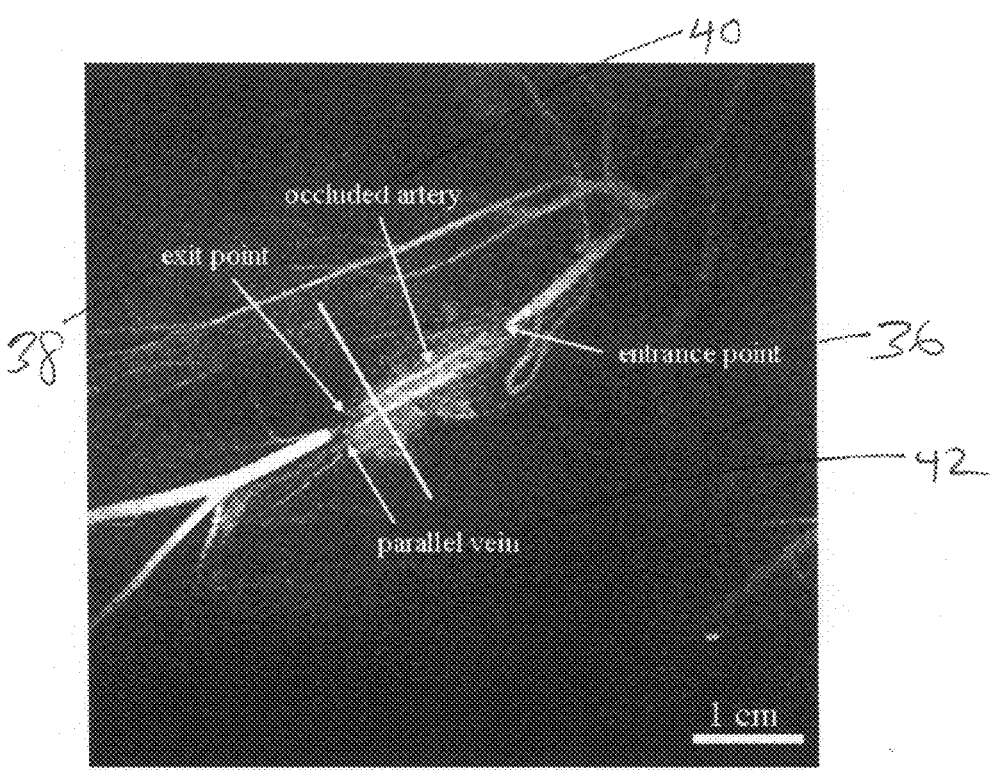
FIG. 5 shows MR images. Maximum intensity projection (MIP) from the 3D map representing signal difference pre-vs post-injection of Gd-DTPA for the CTO at: (a) 6 weeks and (b) 12 weeks. Original images were acquired with a 3D spoiled gradient echo sequence on a GE 3T scanner with 3×5 cm surface coil over the lesion. In-plane resolution of the data set is approximately 270 um while through-plane resolution is 1 mm.
Figure 5B:
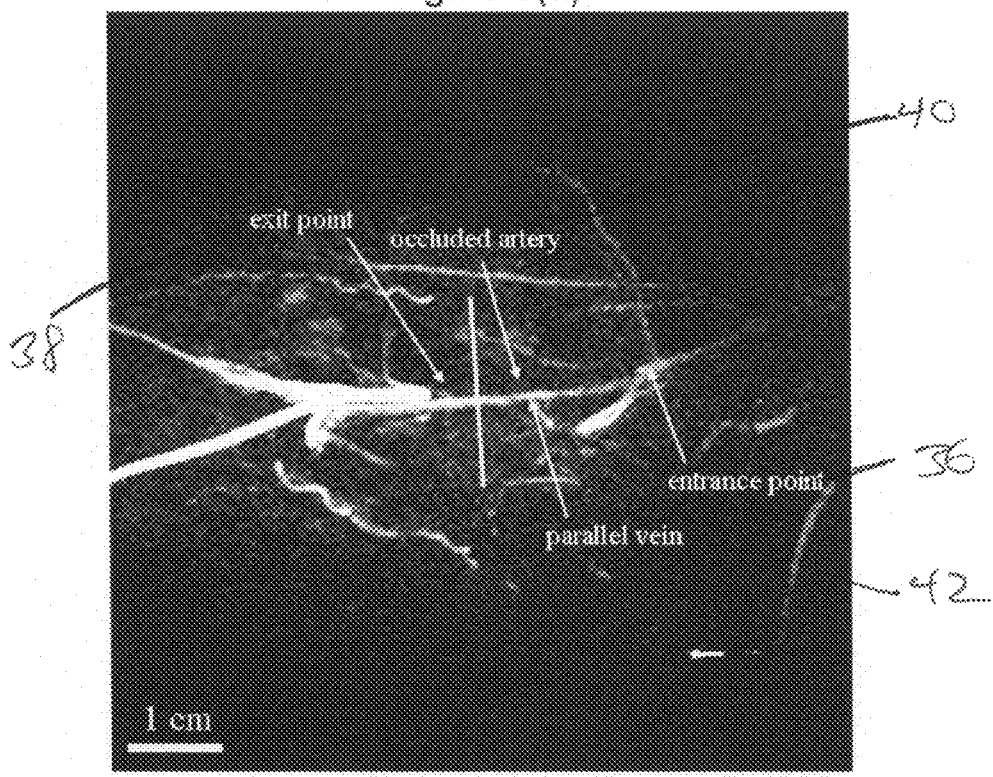
Figure 6A:
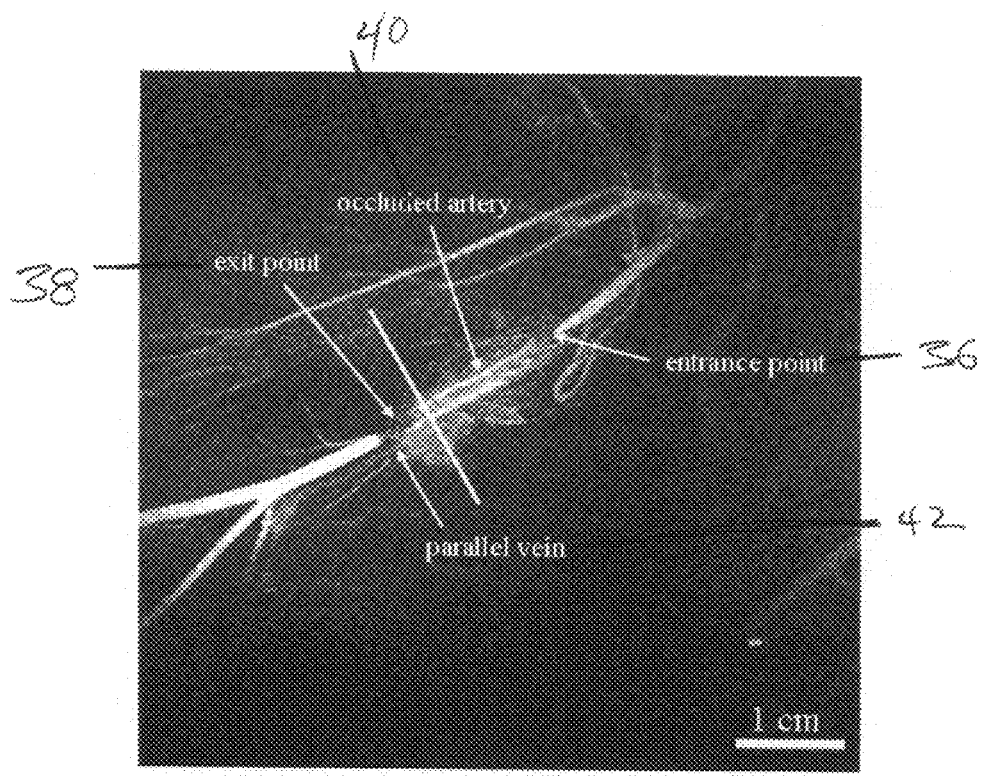
FIG. 6 shows regions of interest used for calculation of Gd-DTPA distribution volume score in various regions are shown on contrast-enhanced images used for these calculations at: (a) 6 weeks; and (b) 12 weeks. Acquisition parameters for these images were the same as those described for FIG. 5.
Figure 6B:
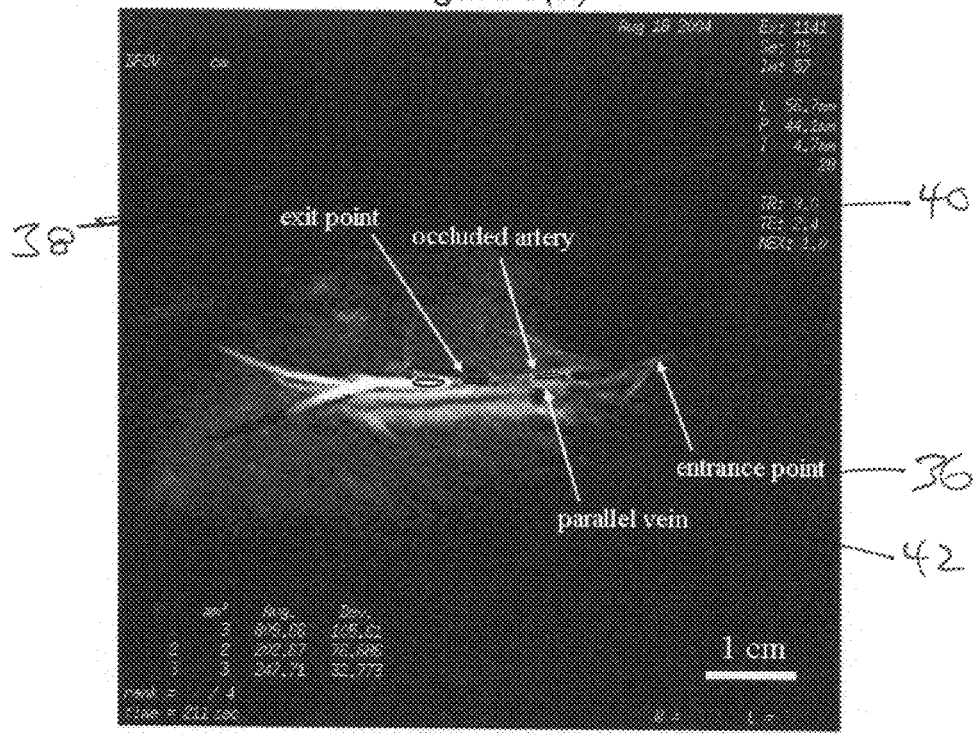

Our studies have indicated that CTO can be imaged and characterized with MR imaging. An example is shown in FIGS. 4(a) and (b), a CTO imaged at 6 weeks and 12 weeks, respectively. Contrast angiography at both time points failed to show flow in the CTO, although it showed an increase in the CTO length over time. This is indicated by the increased distance between the entrance region 36 and the exit region 38 of the CTO. MR imaging with Gd-DTPA (Omnican, Nycomed), showed presence of the contrast reagent within the body of CTO, but not at the entrance region 36 and exit region 38, at both time points, as indicated in FIGS. 5(a) and (b). The arterial anatomy for the occluded artery 40 shown in these figures is similar to that seen in the contrast x-ray angiogram. A parallel vein 42 (more evident in FIG. 5(b)) can be seen below the artery since MR is more sensitive to contrast reagent than is x-ray. This is consistent with perfusion and vascular channels. However, MR showed distinctive differences. At 6 weeks, there were two longitudinal channels at the edges of the lumen as well as diffuse signal in central and surrounding regions. At 12 weeks, the longitudinal channels were no longer present and the diffuse signal was diminished. Using, T1-weighted signal changes with Gd-DTPA, we estimate the percentage of tissue volume occupied by the agent ("distribution volume score") in the centre ("body") of the CTO was 18% and in the exit region was 4% at 6 weeks. At 12 weeks, the distribution volume score in the body had decreased to 3% while the exit region had a relatively constant value of 6%. Regions of interest for these measurements are shown in FIGS. 6(a) and (b). As mentioned above, the entrance point 36 and exit point 38 represent the main obstacle to crossing with the guide-wire, while the central body of the CTO offers far less resistance. Furthermore older lesions offer greater resistance. The volume distribution of Omniscan, a gadolinium based extracellular contrast agent four seconds after injection is related to the directly filled microvasculature and interstitial volume within the occluded vessel. It was thus hypothesized that distribution volume score relates positively with vascularity and ease of crossing. The longitudinal pattern and higher distribution volume present at 6 weeks could be due to either microvessel formation (and thus a direct path through most of the CTO) or increased extracellular space due to inflammation or ECM composition, which are important stimuli for microvessel formation. Since Gd-DTPA is distributed in the extracellular space, rather than exclusive to the vascular space, both are possibilities.

Figure 7A:
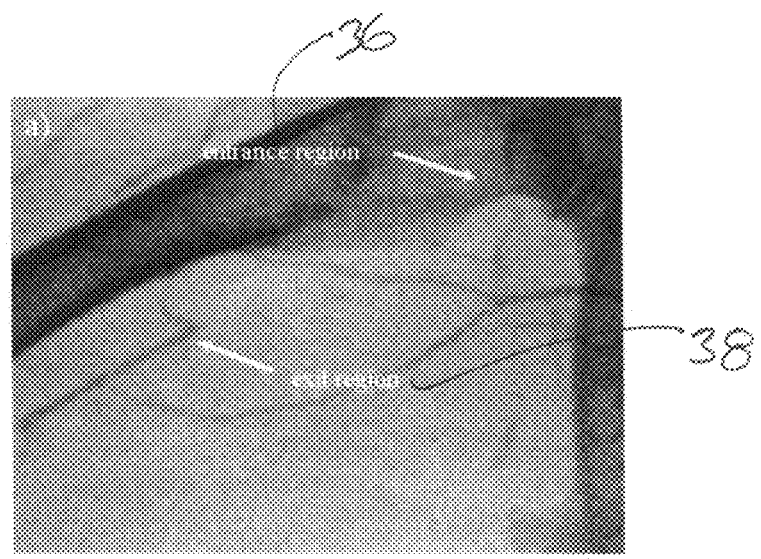
FIG. 7 shows: (a) an X-ray angiogram of a chronic total occlusion at 12 weeks; (b) 3D MIP of the same occlusion from the difference image determined by subtracting MRI signal post Gd-DTPA injection from pre-injection signal; (c) low resolution (86 microns) microCT image of the same region. All images including microCT depict various collateral branches bridging the occlusion.
Figure 7B:
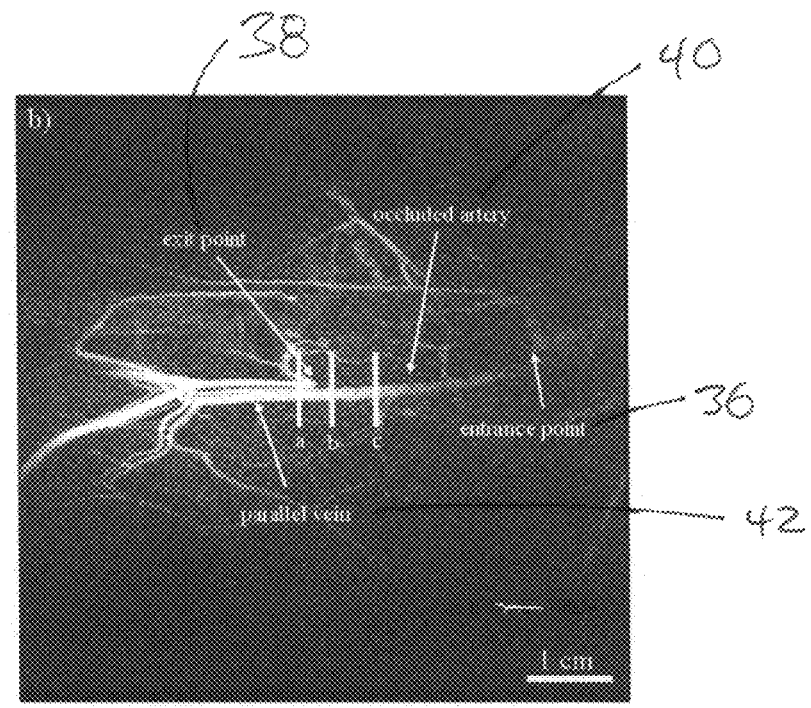
Figure 7C:
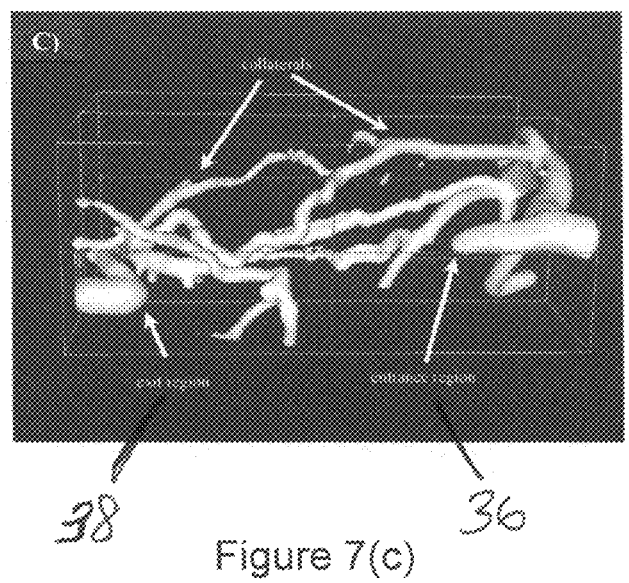
Figure 8:
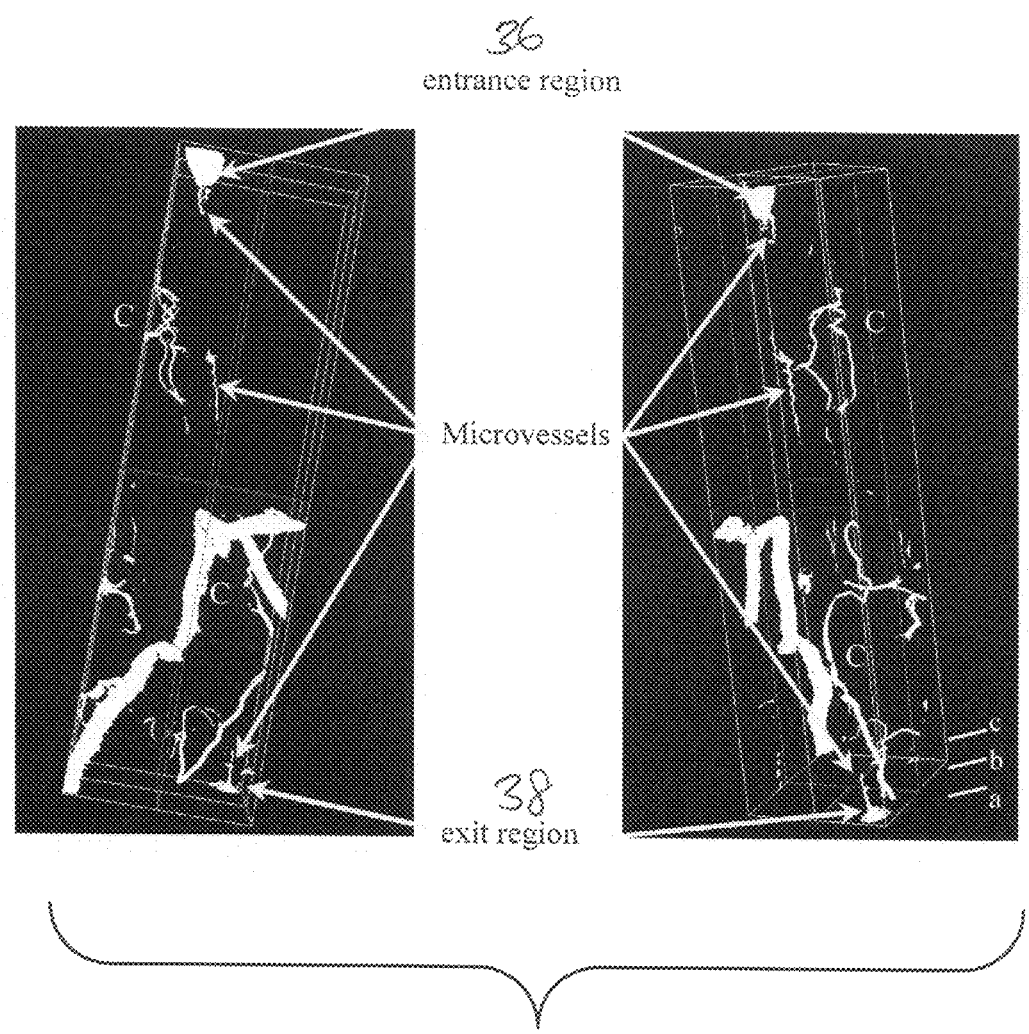
FIG. 8 shows a high-resolution (17 microns) microCT image of the occluded region depicted in FIG. 7. Exit and entrance regions and collateral vessels can be seen as well as microvessels within the occlusion. "Microvessels" at the entrance and exit may also be narrowed extensions of the original lumen. Slice positions of FIGS. 9(a) to (c) are indicated as labelled lines a to c, respectively.
Figure 9:
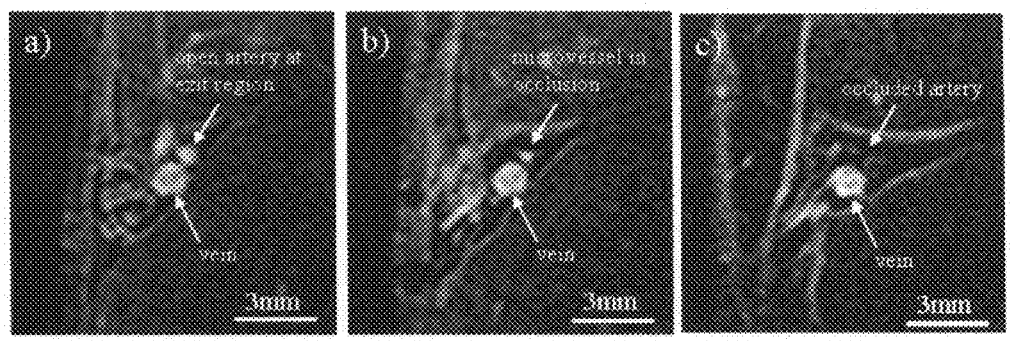
FIGS. 9(a), (b) and (c) show a cross-sectional MRI difference images (from data sets similar to FIG. 8(b)) depicting Gd-DTPA distribution at various slices through the occluded artery in FIG. 9. The positions of the cross-sections with respect to the exit region are indicated in FIGS. 8(a), (b) and (c) as lines a, b, and c, respectively.

As can be seen in FIGS. 7 to 9, micro-CT can be used to demonstrate actual microchannels within the chronic total occlusion. Low resolution micro-CT (86 microns), shown in FIG. 7C, is very useful for showing collateral vessels outside the lumen but may not detect intaluminal microvessels. However, the use of higher resolution micro-CT imaging (17 microns), shown in FIG. 8, is able to demonstrate very small microvessels just distal to the entrance site and just proximal to the exit site of the CTO. In FIG. 9, Gd-DPTA can be seen in MR image immediately proximal to exit region, indicating the presence of a microvessel just before the exit region. However, immediately proximal to this microvessel, no Gd-DPTA is evident in the lumen of the CTO, indicating absence of microvessel.

Figure 4B:
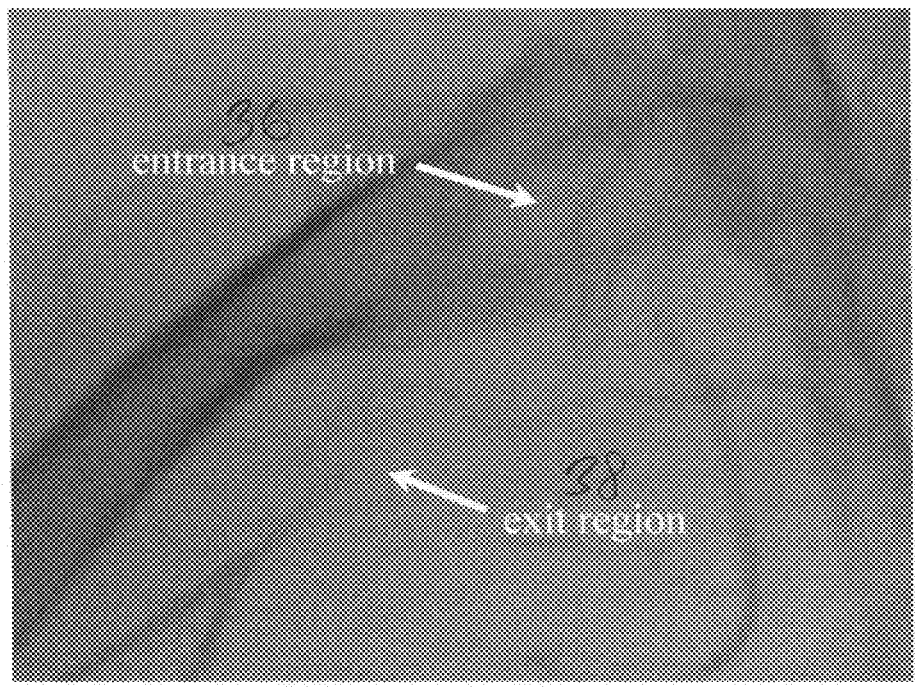
Figure 10A:
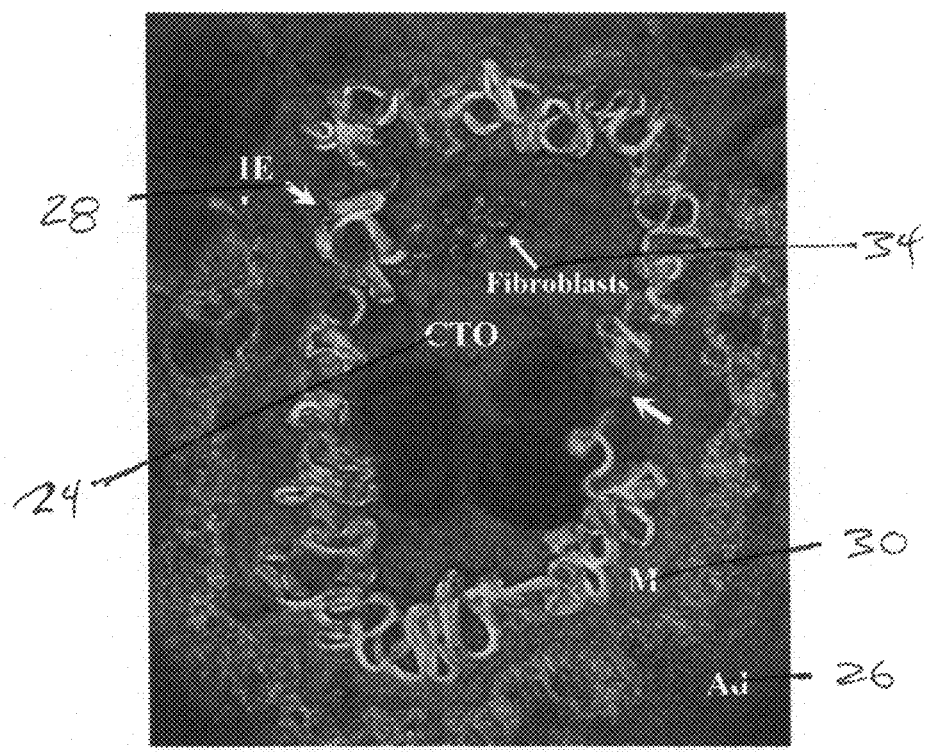
FIG. 10 shows: (a) and (b): Confocal fluorescent images; (c) and (d): H&E stained arterial sections from a 12-week old CTO at 4 hours after injection of CMTMR-labeled rabbit fibroblasts. CMTMR-labeled rabbit fibroblasts appear dark color in (a), (b), (c) and (d) at different levels of the CTO.
Figure 10B:
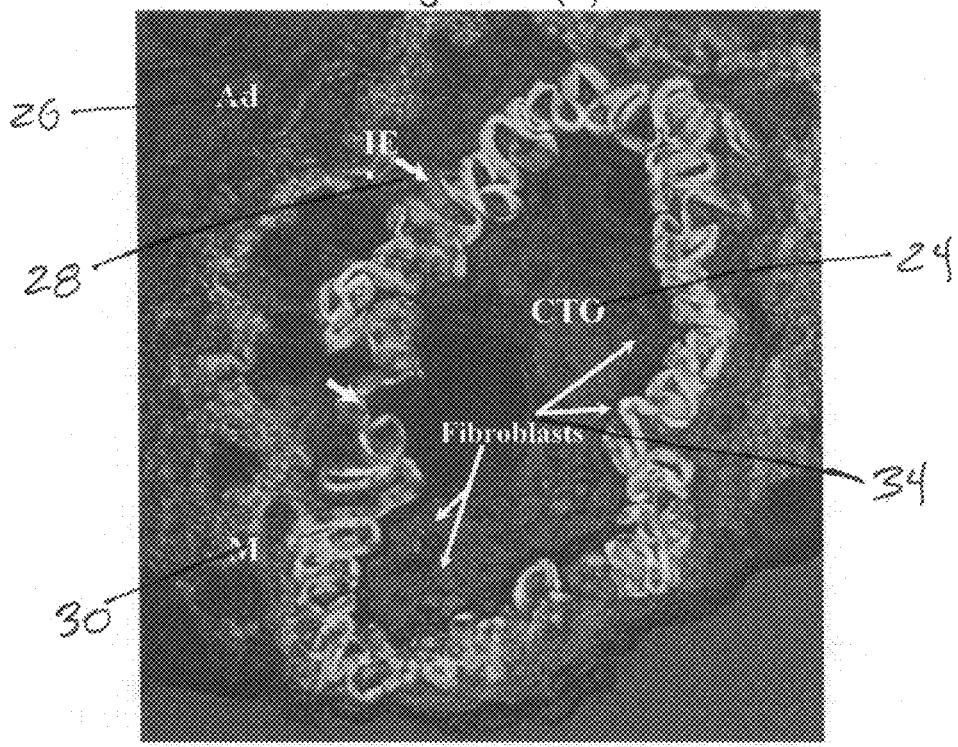
Figure 10C:
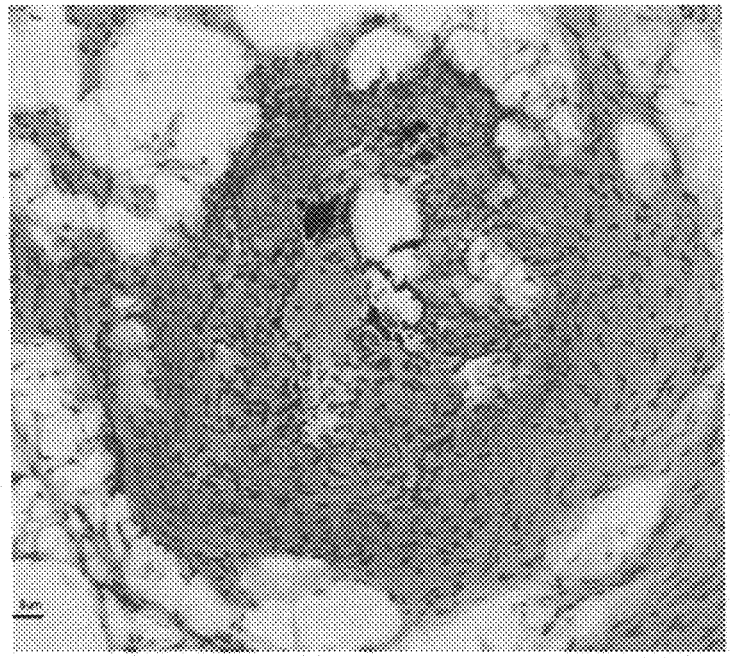
Figure 10D:
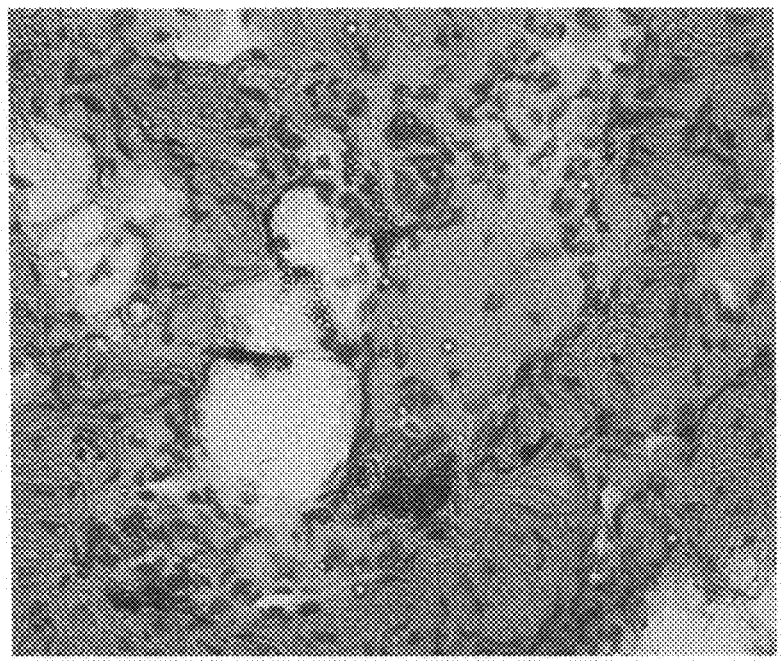

This invention includes a strategy to improve guide-wire crossing rates in CTO by increasing intraluminal microvessel formation. Initial studies established the feasibility of gene therapy using a cell-based approach. This was accomplished by delivery of rabbit fibroblasts (FB) that have been labeled with the fluorophore chloromethyl trimethyl rhodamine (CMTMR), a red cell-tracker dye that is only present in viable cells, through the wire-port of an over-the-wire angioplasty balloon catheter, as previously described for collagenase infusion (85). CMTMR affords a method of detecting ex vivo-labeled FB because the molecule undergoes irreversible esterification and glucoronidation after passing into the cytoplasm of a cell to generate a membrane impermeable final product. This active fluorophore is unable to diffuse from the original labeled cell into adjacent cells or structures, and may be detected in vivo for several months. At 4 hours after injection, we found nests of these fluorescent-labelled FB at several levels of the CTO (FIG. 10), showing reasonable residency times for local gene expression. CMTMR-labeled rabbit fibroblasts 34, appeared as dark color in FIGS. 10(a), 10(b), (c) and (d) in a 12-week-old CTO at 4 hours after injection. These cross-sections are located approximately 6-10 mm from the beginning of the occlusion. The internal elastic lamina 28 is evident in FIGS. 4(a) and 4(b) due to autofluorescence.

VEGF has been shown to induce angiogenesis in experimental vascular models (88-90), and is currently in clinical trials for myocardial ischemia and peripheral vascular disease with promising preliminary results (91-94). Studies have shown high levels of VEGF expression at the site of cell delivery and engraftment with cell-based delivery of smooth muscle cells (95) in a pulmonary hypertension model. An additional reason for a cell-based strategy in establishing the feasibility of inducing angiogenesis using the animal model is the relatively small number "native" cells in the collagen-rich CTO at 12 weeks for transfection by other methods.

Feasibility studies on angiogenic therapy using local delivery of VEGF-transfected smooth muscle cells to increase intraluminal microvessels in chronically occluded arteries were thus conducted. First, venous smooth muscle cells were grown in culture and the culture expanded to obtain a sufficient number of cells for delivery. This took approximately 2 weeks. The external jugular veins of rabbits were removed, and venous smooth muscle cells were placed in culture using an explant method.

The smooth muscle cells were transfected with the human VEGF transgene. Smooth muscle cells from passage#2 were transfected with VEGF plasmid or null plasmid in serum- and antibiotic-free DMEM using SuperFect® Transfection Reagent (QIAGEN) and incubated for three hours. Media containing plasmid was removed and cells were washed twice with PBS. Then 5 ml DMEM containing antibiotic and 10% fetal calf serum was added and incubated for 48 hours. At 24 hours after transfection, VEGF ELISA was performed on conditioned media using Human VEGF Immunoassay kit (R&D Systems) to ensure VEGF protein expression (range 1.73-1.82 ng VGF/ml). At 48 hours after transfection, smooth muscle cells were trypsinized and washed with phosphate buffered saline (PBS) once (2000 rpm, 2 min). Cells were resuspended in 0.5 ml PBS and kept on ice before injecting to the animals.

The VEGF-transfected cells which were in suspension were then locally delivered through the wire port of an angioplasty balloon catheter. Each rabbit was treated with venous smooth muscle cells that originated from that particular rabbit's jugular vein. Rabbits were anesthetized and a 4F arterial sheath was inserted into the left side carotid artery. An over-the-wire angioplasty balloon catheter was advanced under fluoroscopic guidance until it was immediately adjacent to the femoral artery total occlusion. The angioplasty balloon was inflated 4 atmospheres to prevent any backflow and loss down sidebranches. The guide wire was removed from the guide wire port and the suspension (0.5 ml) containing the VEGF-transfected smooth muscle cells was slowly injected through the wireport to fill the small space between the inflated balloon and the chronic total occlusion. The catheter was then flushed with 0.5 ml of 0.9% saline to ensure that no cell suspension was still in the catheter. The angioplasty balloon was left inflated for 45 minutes and then the angioplasty balloon was deflated and removed. The animals were then allowed to recover.

After about 3 weeks, to permit formation of microvessels, the rabbits underwent MRI imaging with Gd-DTPA. Animals were sacrificed after MRI scanning and microfil was injected under the pressure of 80 mm Hg via abdominal aorta to the occluded arteries for micro CT examinations. The arterial segments were removed and the tissue was fixed in 10% formalin, processed and then stained with hemotoxyline and eosin (H&E) and movat stains.

Figure 11A:
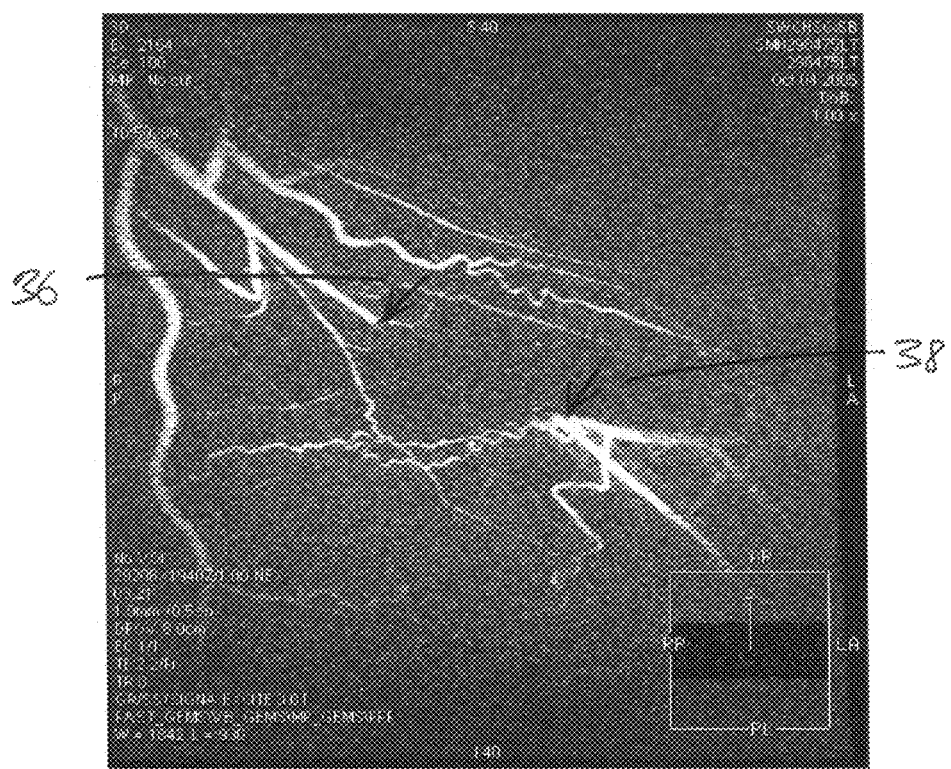
FIG. 11(a) shows a MR image of a CTO in a rabbit left femoral artery. The CTO is approximately 9 months old. This untreated CTO did not receive infusion of VEGF transfected smooth muscle cells. MR imaging after Gd-DTPA did not show any evidence of flow within the CTO.
Figure 11B:
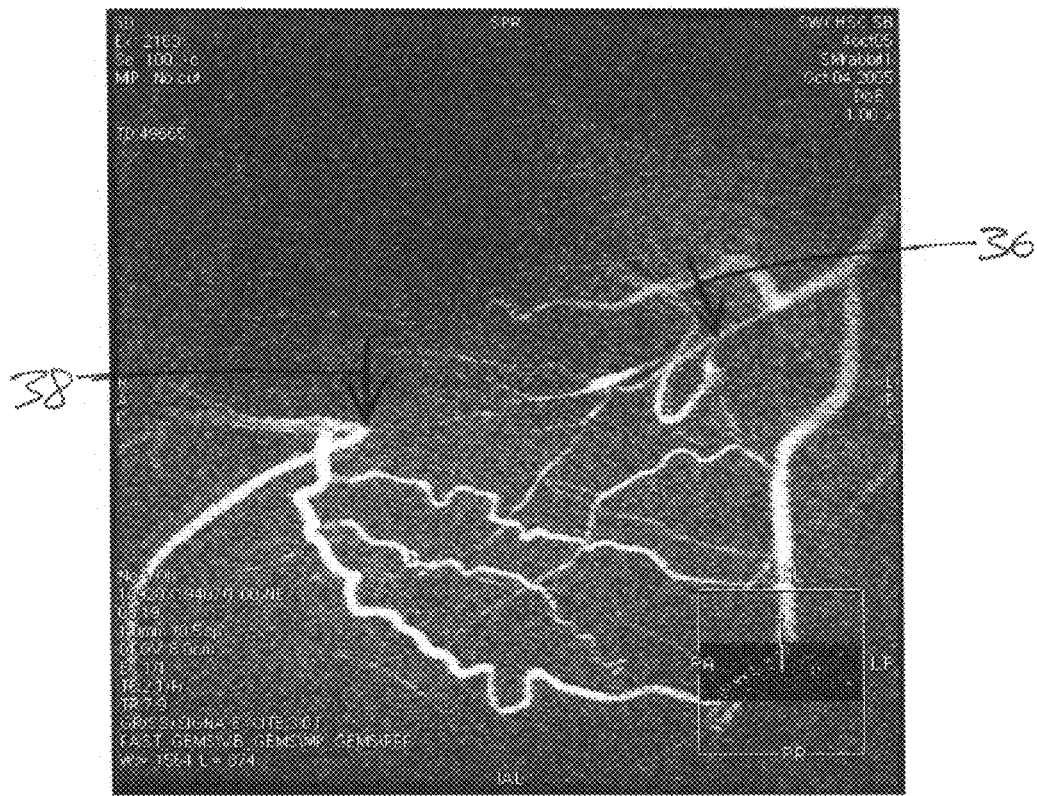
FIG. 11(b) shows the right femoral artery from the same rabbit as FIG. 11(a). At 8 months, this CTO was treated with $3 \times 10^5$ VEGF-transfected smooth muscle cells. The presence of gadolinium uptake in the lumen of the chronic total occlusion of FIG. 11(b) (arrowheads) (but not in the untreated CTO shown in FIG. 11(a)) is evidence of microvessel formation within the occluded lumen of the CTO establishing the increased probability of successful crossing of the occlusion.

Results are shown for a rabbit CTOs that were approximately nine months old at the time of sacrifice in FIGS. 11(a), 11(b) and 11(c). FIG. 12(a) is an MR image after Gd-DPTA injection of the CTO of the left femoral artery, the occlusion not having been treated with smooth muscle cells. FIG. 11(b) is an MR image after Gd-DPTA injection of the right femoral artery from the same rabbit, having an occlusion that had been injected with $3 \times 10^5$ VEGF-transfected smooth muscle cells at 8 months old and then sacrificed 3 weeks later. The presence of gadolinium uptake in chronic total occlusion of FIG. 11(b) (indicated by arrowheads) is evidence in support of the formation of new vessels therein, establishing the increased probability of successful crossing of the occlusion.

Figure 12:
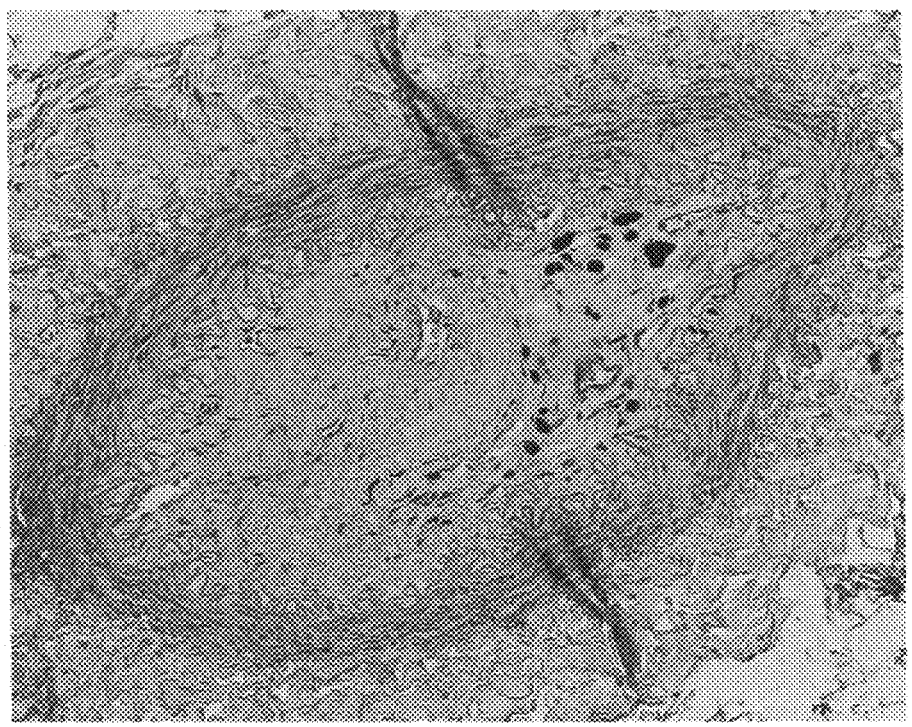
FIG. 12 is from a different rabbit CTO that was also treated with VEGF transfected smooth muscle cells at approximately 7 months old and then sacrificed 3 weeks later. The movat-stained arterial cross-section shows the CTO (24), which has many microvessels that are filled with black colored microfilm, again indicating microvessel formation that is important to successful guidewire crossing.

FIG. 12 is from a different rabbit CTO that was also treated with VEGF transfected smooth muscle cells at 8 months old and then sacrificed 3 weeks later. The movat-stained arterial cross-section shows the CTO (24), which has many microvessels that are filled with black colored microfilm, again indicating microvessel formation that is important to successful guidewire crossing.

Results of this study indicate that VEGF-treated chronic total occlusions demonstrated microvessel formation therein. MR images in several VEGF treated CTOs have shown gadolinium uptake within the proximal and mid portion of the CTO, as illustrated in FIG. 11(b). This contrasts with an untreated CTO of the same animal, illustrated in FIG. 11(a). Such untreated CTOs, from this study as well as previous MRI studies of CTOs have shown essentially no gadolinium uptake in chronic total occlusions at 12 weeks or beyond. The presence of gadolinium uptake in chronic total occlusions over 8 months is evidence for new vessel formation. These microvessels in VEGF-treated CTO were confirmed in Movat-stained stained arterial sections which showed multiple vascular channels, shown in FIG. 12. These vascular channels were filled with microfilm which was used for microCT imaging. Microfil identifies sites of blood flow within the CTO, indicating that these microchannels were functional.

VEGF Delivery by Microspheres into Experimental Chronic Total Occlusions

A second approach to VEGF delivery into a chronic total occlusion was tested, a biodegradable polymer, 50:50 PLGA (polylactic and glycolic acid) as a drug delivery system for VEGF. The spheres were fabricated using a double emulsion technique (water-oil-water), with average size of 20 microns, shown in FIGS. 13(a), 13(b) and 13(c). The possibility of creating the sphere was initially established by preparing spheres filled only with water. Then bovine serum albumin (BSA) containing spheres, and then microspheres containing both VEGF and BSA were prepared. The BSA acts as a carrier protein, helping to create channels through which the VEGF can diffuse out of the spheres.

In the case of BSA/VEGF spheres, 17 mg of BSA was added to 200 uL of water. This volume was used to dissolve 5 micrograms of VEGF. The whole protein mixture was then pipetted into the dissolved polymer (dissolved in chloroform) to create droplets of protein mixture within the polymer solution. The polymer solution was then made into beads with the protein droplets incorporated into the beads. The batch of spheres produced 71.6 mg of usable beads, which were of reasonably uniform size as determined by light microscopy. An injection volume into the chronic occlusion of about 1 ml has been found to be successful, and it was found possible to dissolve 15 mg of the beads into this volume without making the solution too viscous for injection. Based on studies with BSA incorporation into the beads, it was estimated that approximately 30% of the VEGF is incorporated into the beads, which translates into 0.32 ug of VEGF in the injection of 15 mg of beads.

Studies were carried out using six rabbits with chronic total occlusions of >12 weeks. Animals were either treated with control injections of saline (three animals) or with the BSA/VEGF microspheres (three animals) as follows. After angiographic confirmation of the occlusion, an over-the-wire angioplasty balloon catheter was placed on a 0.014" guide wire and advanced to the proximal part of the occlusion. The balloon was inflated to prevent back-flow of the solution. The guidewire was removed from the catheter. Then a 1 ml solution containing 15 mg of the microsphere beads was slowly infused over approximately 1 minute through the wire-port of the catheter into the space between the occlusion and the distal tip of the balloon and allowed to diffuse into the CTO. The balloon inflation was maintained for 45 minutes after delivery of the BSA/VEGF microspheres. The rabbits were then returned to the cages for follow-up 3 weeks later. One of the VEGF treated rabbits died early post-operatively for unknown reason, presumably related to the anaesthetic.

The rabbits underwent magnetic resonance (MR) imaging after injection intravenous injection of Clariscan, a contrast agent that stays intravascular and thus provides information about microvascular volume in the CTO. MR imaging was done just before delivery of the BSA/VEGF microspheres and then 3 weeks later. After MR imaging at 3 weeks, and at the time of sacrifice, microfil (an x-ray opaque liquid that sets to form a cast) was injected into the femoral artery just proximal to the occlusion. This is a contrast agent which permits delineation of the vasculature for micro CT scanning, which was done ex-vivo after removal of the chronic occlusion. Samples were then processed for histology and stained with hematoxylin and eosin.

As demonstrated by the images shown in the figures, the two surviving animals that were treated with VEGF microspheres showed evidence of increased flow at 3 weeks post therapy, evidencing new vessel formation. This is based on MR imaging, micro CT scanning and the histology.

Figure 14:
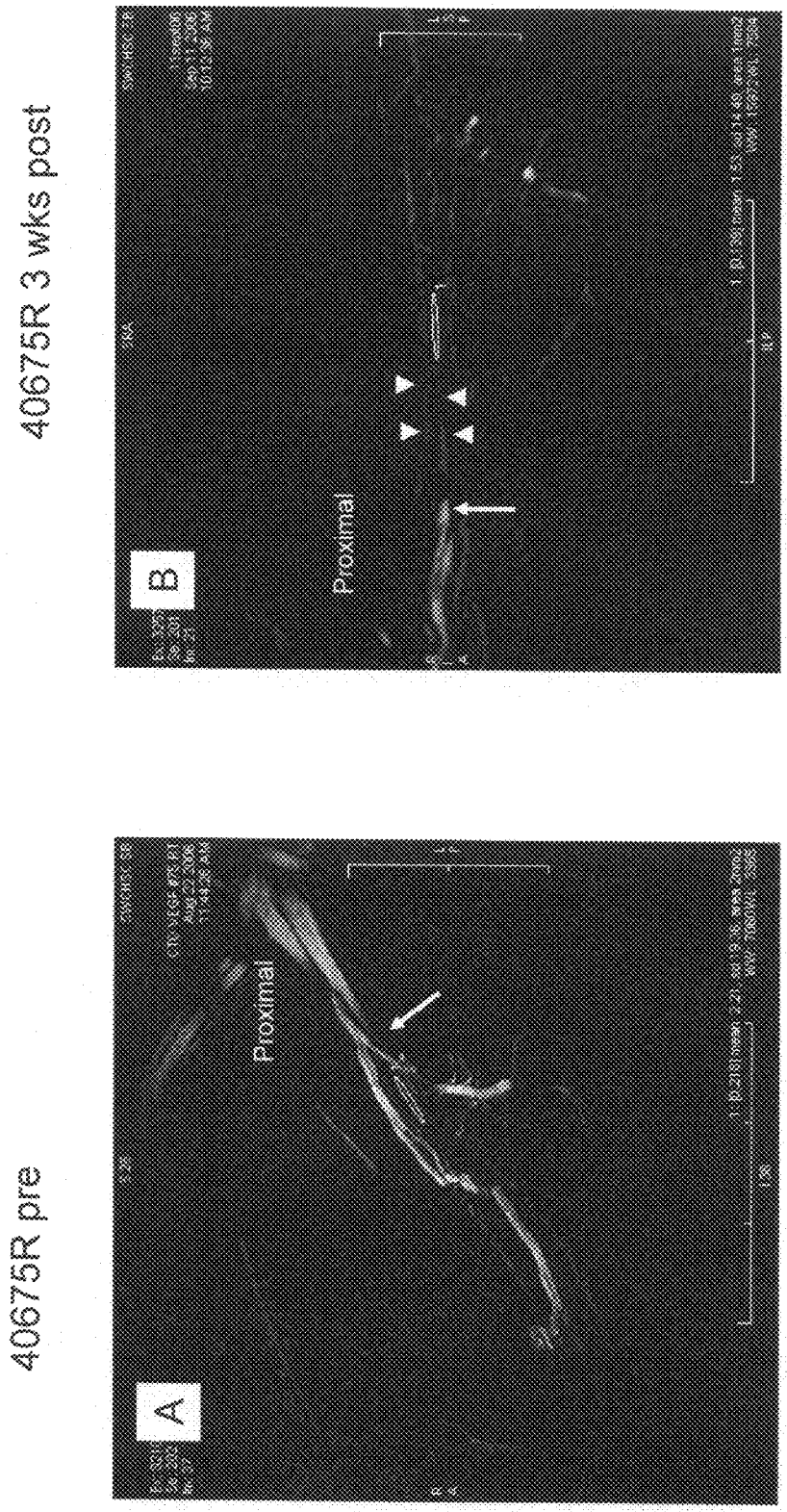
FIGS. 14(a) and 14(b) are magnetic resonance images after injection of clariscan contrast reagent of a femoral CTO treated with the VEGF spheres, shown before (14(a)) and three weeks after (14(b)) treatment.
Figure 15:
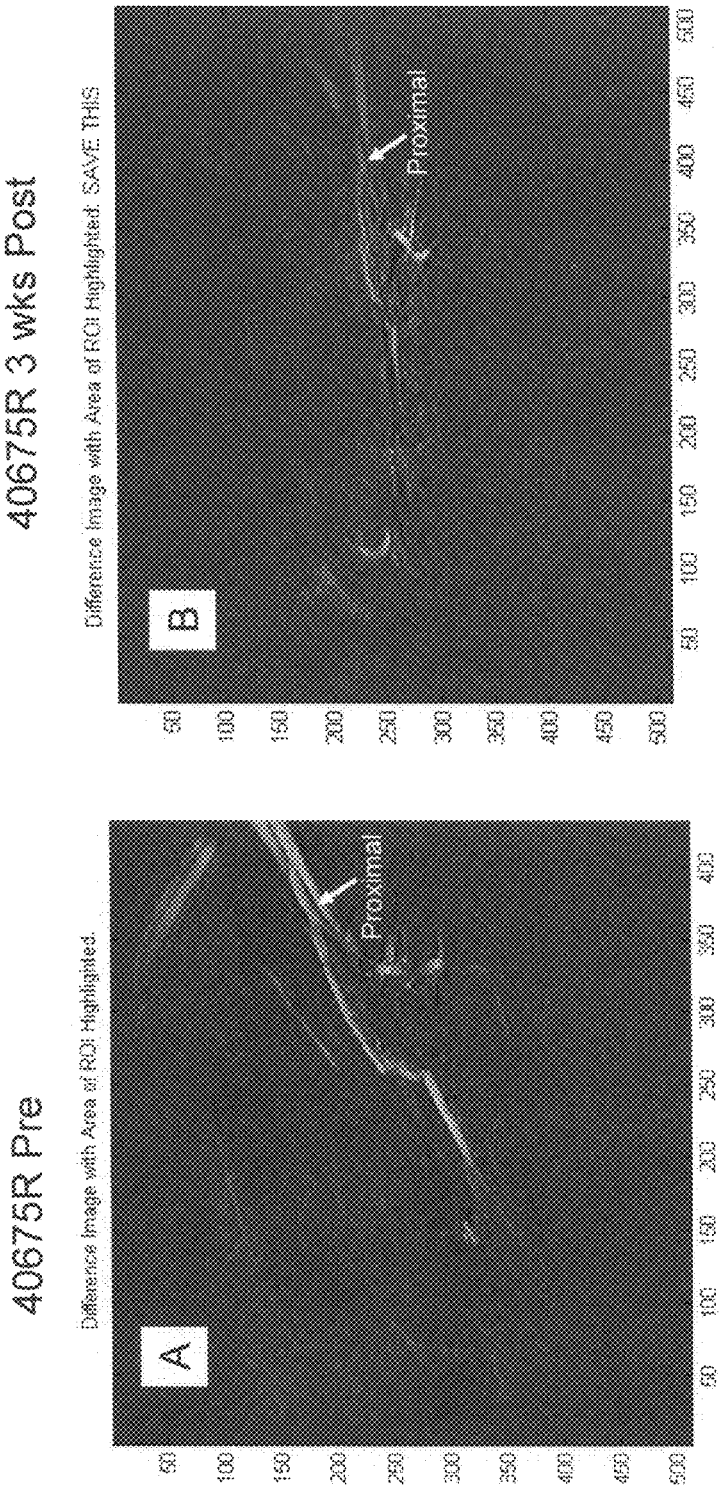
FIGS. 15(a) and 15(b) are MR images after injection of clariscan contrast agent of a rabbit femoral CTO treated with the VEGF spheres. The perfusion analysis was done in a specified region of interest (ROI), indicated in red, in which a quantitative analysis of pixel intensity was performed.
Figure 16:
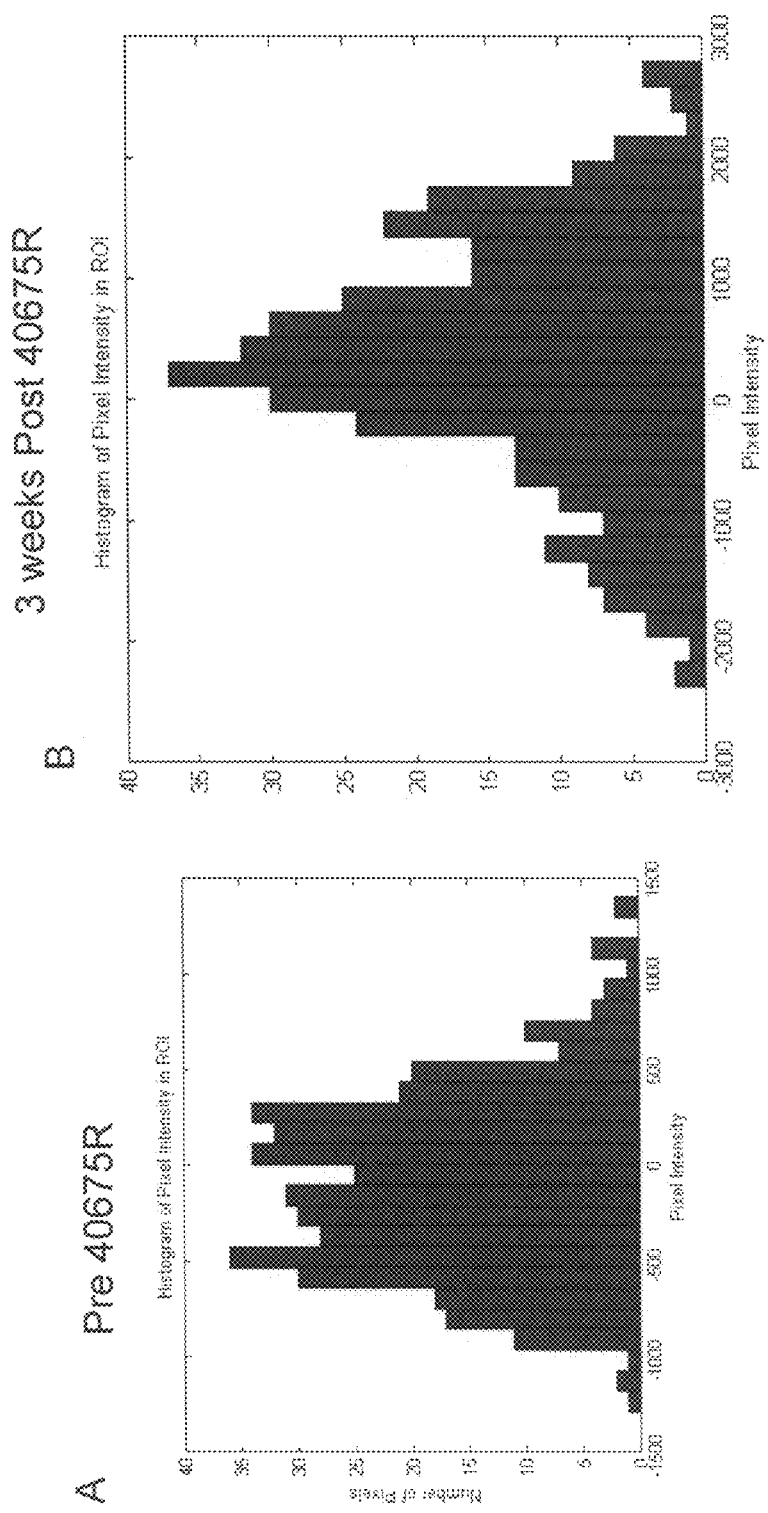
FIGS. 16(a) and 16(b) are pixel counts, showing the difference in pixel intensities in the regions of interest shown in FIGS. 15(a) and 15(b), respectively.

Both of these VEGF-treated animals showed increases in signal intensity beyond the proximal part of the occlusion in clariscan enhanced MR images. In FIG. 14 (rabbit 40675R), there is enhancement of the signal at the periphery of the lumen. This is indicated by the white arrowheads of FIG. 14(b) at 3 weeks after VEGF treatment, within the occluded segment, the proximal border of the occlusion in FIGS. 14(a) and (b) being indicated by the arrows. The region of interest (indicated in red), in which a quantitative analysis of pixel intensity was performed, is shown in FIGS. 15(a) and 15(b). A pronounced increase in the pixel intensity was found at 3 weeks in the occluded segment, i.e., the number of pixels with higher intensity increased compared to pre treatment.

Figure 17:
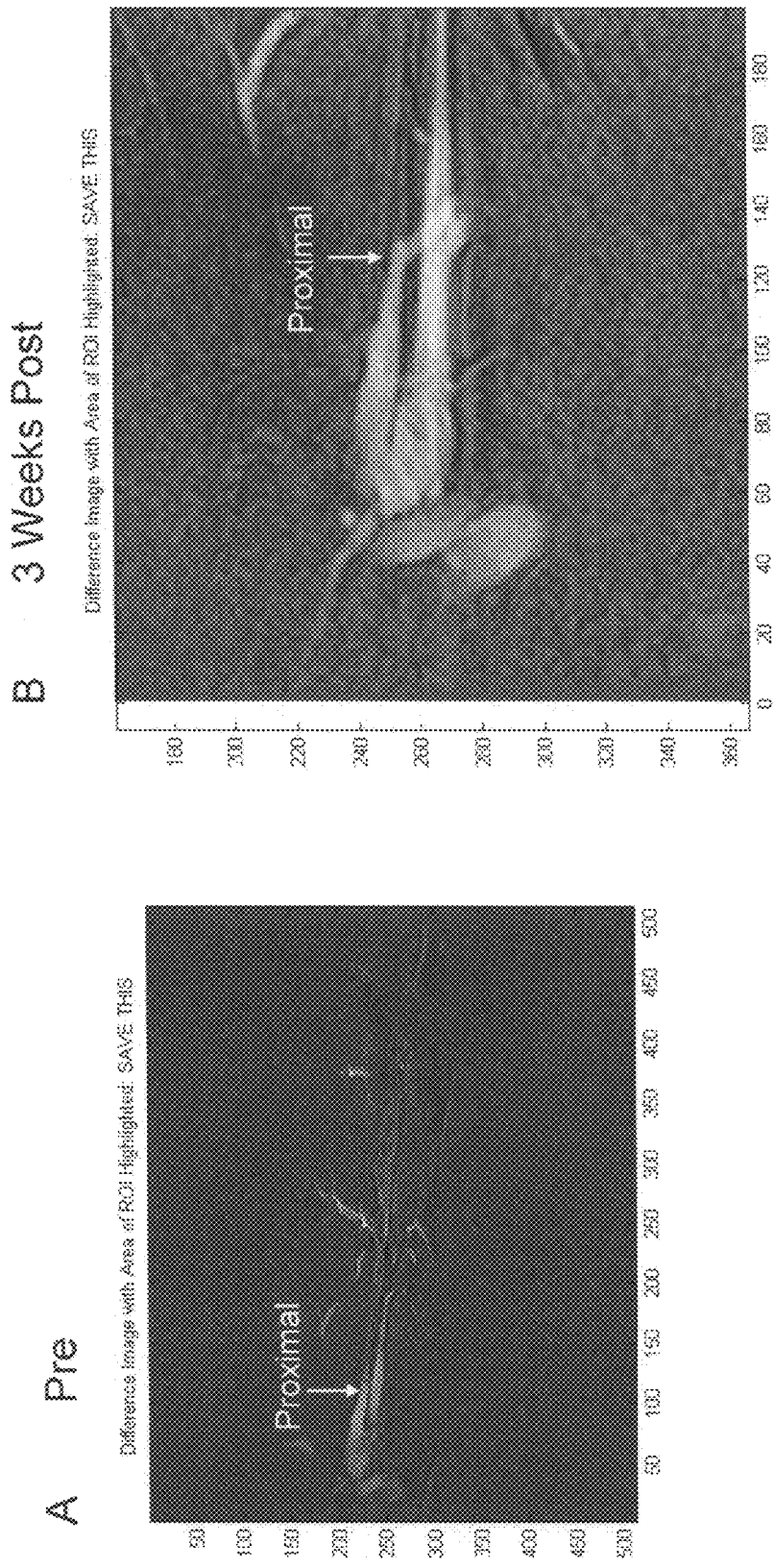
FIGS. 17(a) and 17(b) are similar to FIGS. 15(a) and 15(b), respectively, for a second rabbit. Again, the proximal border of the occlusion is indicated by an arrow and the ROI appears as red color just beyond the proximal border of the occlusion.
Figure 18:
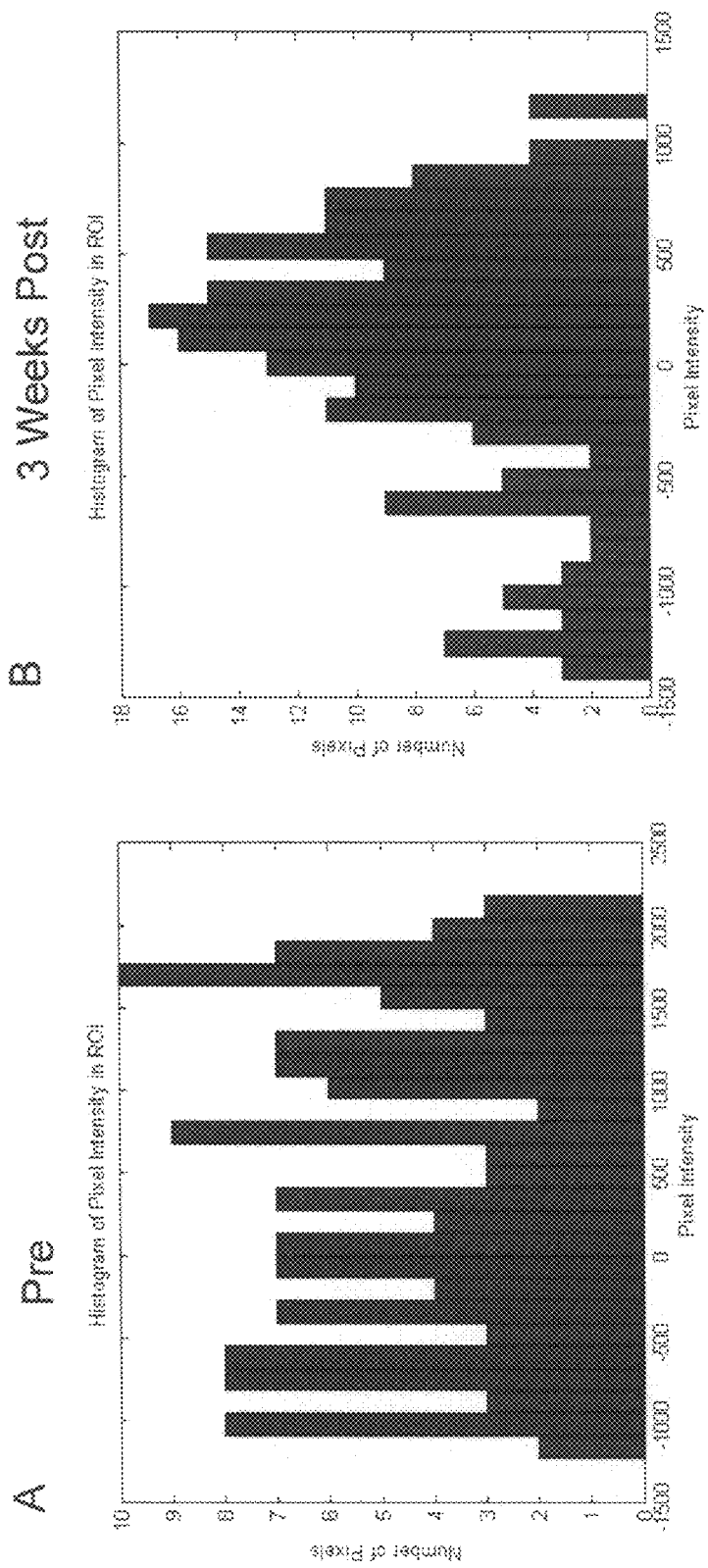
FIGS. 18(a) and 18(b) are similar to FIGS. 16(a) and 16(b), respectively, for a second rabbit.

A similar analysis for the second VEGF treated rabbit [40676L] is shown in FIGS. 17(a), 17(b), 18(a) and 18(b). The region of interest (ROI) just beyond the proximal part of the occlusion is indicated in FIGS. 17(a) and (b). The analysis of pixel density within the ROI, shown in FIGS. 18(a) and (b), again shows an increase in the number of pixels with higher intensity in the 3 week MR image compared with the pretreatment MR image.

Figure 19:
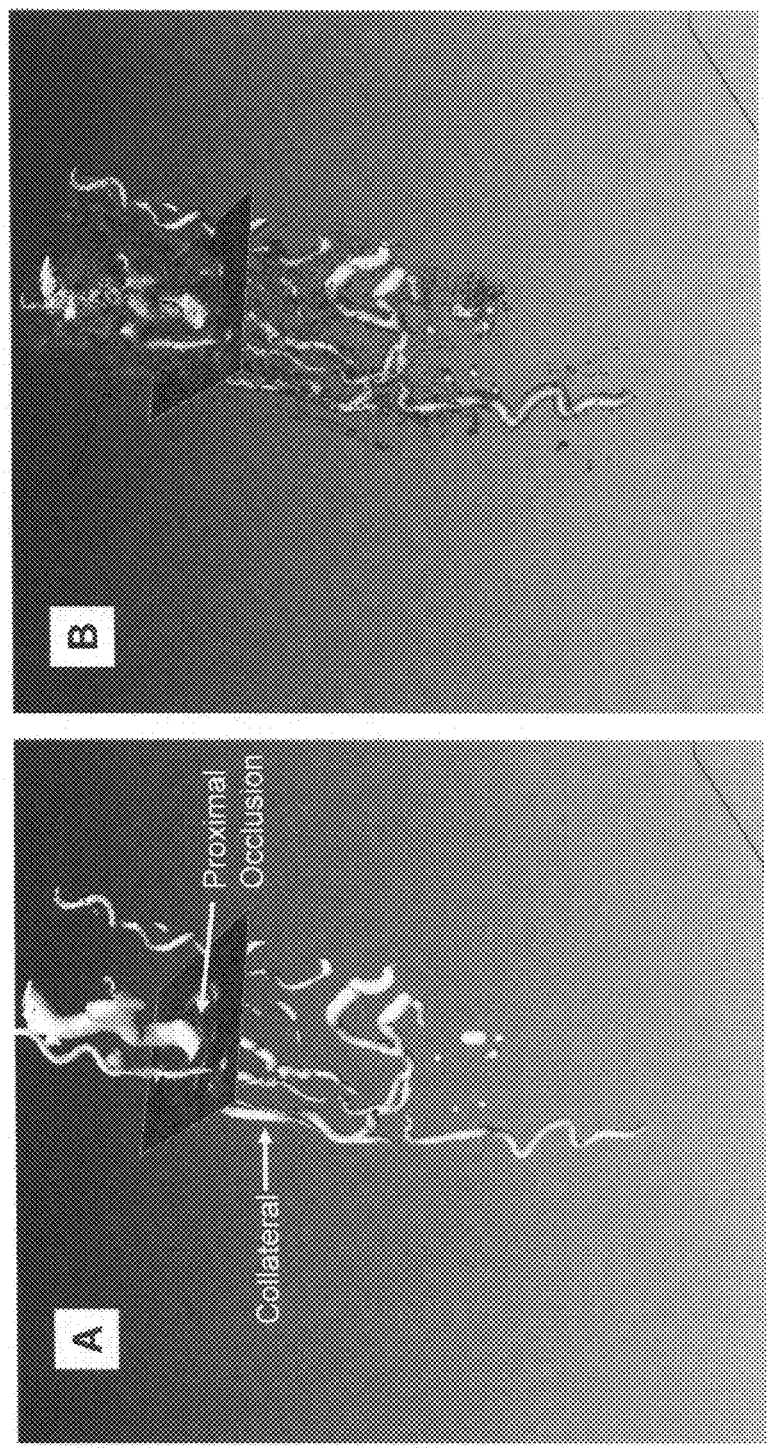
FIGS. 19(a) and 19(b) are maximum intensity projection (MIP) images obtained by micro-CT of a VEGF treated artery at 3 weeks after VEGF treatment. Microfil was injected prior to sacrifice of the animal. After removal of the artery, the micro-CT imaging was preformed for detection of vasculature using the microfilm as a contrast reagent.
Figure 20:
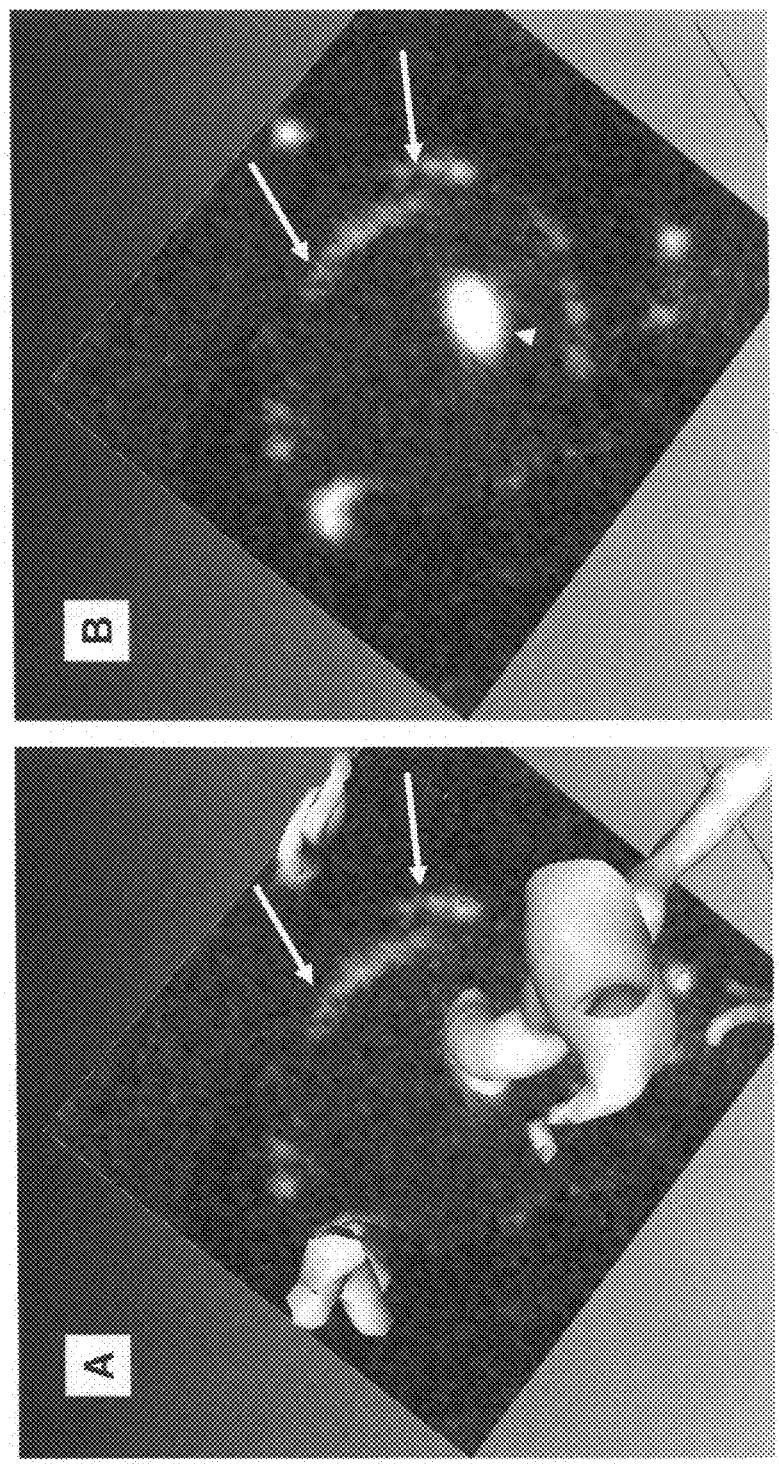
FIGS. 20(a) and 20(b) are cross-sections of micro-CT images at the proximal border of the occlusion.
Figure 21:
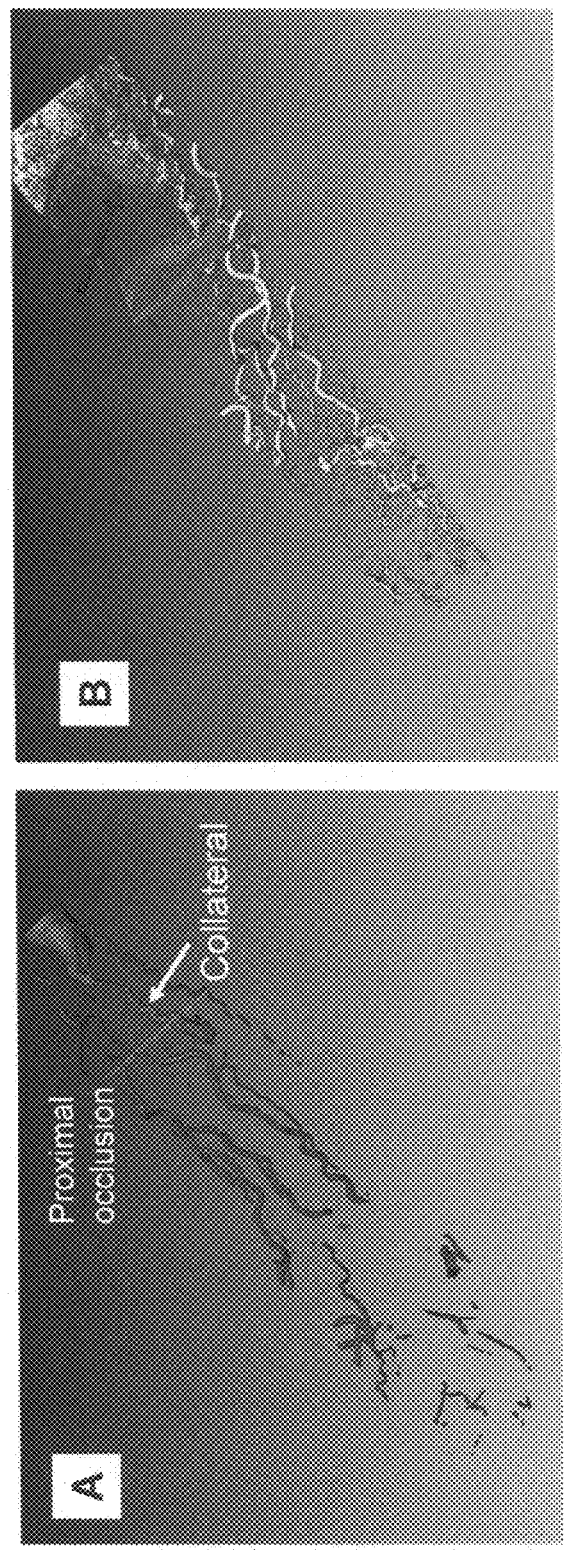
FIG. 21 (a) only represents the high sensitivity threshold parameters detection, while FIG. 21(b) includes the lower sensitivity threshold detection for identifying smaller, finer microvessels.

Micro-CT images are shown in FIGS. 19 to 23. The VEGF-treated arteries are shown in FIGS. 19 to 21 and the control saline treated FIGS. 22 and 23. FIG. 19(a), [rabbit40675R], shows detection of a lower sensitivity signal of the main vasculature, which shows up as yellow color in well-defined vessels. The proximal part of the occlusion and a collateral vessel outside the plane of the occluded vessel are labeled. In FIG. 19(b), higher sensitivity detection was used which recognizes weaker signals in the micro-CT, which show up as brownish-red color. These weaker signals represent the smaller, poorly defined, thin-walled vascular channels in the occluded lumen and the medial layer of the vascular wall, that appear to have formed in response to the delivery of the VEGF microspheres. FIG. 20 shows a cross-section of micro-CT at the level of the proximal occlusion, which is indicated by the yellow vessel in the center of the vessel in FIG. 20(a) and by an arrowhead in FIG. 20(b). The weaker signals, again reflecting smaller, thin-walled vessels, show up as enhancement in the peripheral aspect of the arterial lumen, labeled by arrows. The increase in this network of smaller vasculature is present in the initial part of the occlusion, about the first third of the occlusion. Similar results were seen for the second VEGF-treated rabbit [rabbit 40676L], as can be seen in FIG. 21. In FIG. 21(a), the proximal occluded vessel (indicated by black arrow) and larger extravascular collaterals appear as red, while in FIG. 21(b), they appear as white. The weaker signals detected in FIG. 21(b) appear as a brownish color. This vasculature is rather poorly defined and extends into the proximal part of the occluded vessel.

Figure 22:
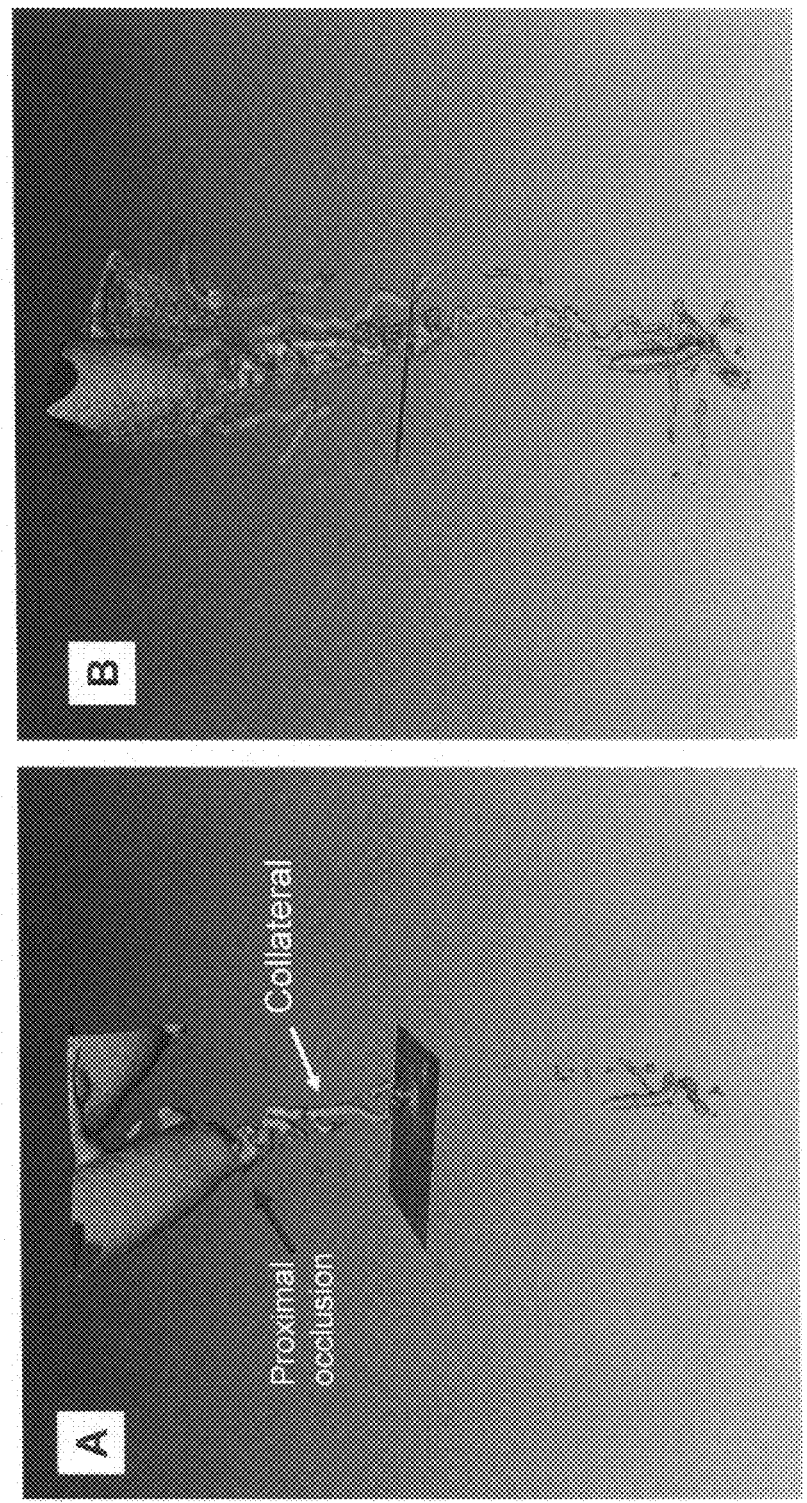
FIGS. 22(a) and 22(b) are micro-CT images showing a control (saline) treated occlusion in a different rabbit.

In contrast, a control treated vessel (saline injection) is shown in FIGS. 22 and 23 [Rabbit 40671L]. The main vessel just before the site of proximal occlusion and a well-formed intraluminal collateral are shown (orange color). In FIG. 22(b), a weaker signal adjacent to the intraluminal microvessel also shows up as a blue color. This also appears as well-defined intraluminal microvessel, which was not detected at the threshold sensitivity used in FIG. 22(a). However this well-developed intraluminal microvessel does differ in appearance from the poorly defined, fine-mesh, network of microvasculature evident within the occluded segment described above in FIGS. 19 to 21. In FIG. 23, a micro-CT cross-section of the occlusion just beyond the proximal part of the occlusion, fails to show enhancement in the peripheral aspect of the arterial lumen as described above for FIG. 20, indicating an absence of microvascular formation.

The histology of the two VEGF-treated arteries is shown in FIGS. 24 [rabbit40675R] and 25 [rabbit 40676L]. Thin-walled vascular channels containing red blood cells (dark pink) and serum (light pink) are present in the occluded lumen and the adjacent media (indicated by arrows). More developed, presumably older, arterial channels with a formed media were also present, indicated by arrowheads. These thin-walled channels were present in the first part of the occlusion, consistent with the micro-CT and MR images.

In summary, these results show that local delivery of VEGF microspheres directly into the chronic occlusion results in new vessel formation within the occluded lumen and underlying media of the first ⅓ of the occlusion within three weeks.

The use of VEGF to effect angiogenesis and microvessel formation in CTOs has thus been demonstrated. As would be appreciated by those skilled in the art, other methods for inducing angiogenesis are available and could be used as part of this invention. Some such methods may even be found to be more effective or preferable for practical or economic reasons than the approach described herein. These other approaches to induce angiogenesis are intended to be encompassed by the present invention. In the context of this invention, an "angiogenic agent" is an agent, molecule, drug, protein or other factor know to promote angiogenesis and includes both angiogenic and pro-angiogenic factors as they may be known in the art.

Angiogenic or pro-angiogenic growth factors and/or cytokines or combinations of growth factors and/or cytokines of the invention include vascular endothelial growth factor; angiopoietin 1, 2; PDGF, FGF-2, TGF-beta, hepatocyte growth factor, TNF-alpha, endothelium-derived nitric oxide or nitric oxide donors, growth factor receptors (VEGFR-1, VEGFR-2, PDGFR, tie2), and hypoxia inducible factor (HIF) 1-alpha.

Stem cells that originate from embryos, or bone marrow or circulating blood of adults or endothelial progenitor cells (EPC) are also encompassed by the invention. Both cell types are highly angiogenic (95, 96). The angiogenic potential of these cells can be further bolstered by genetic manipulation of the EPC to overexpress angiogenic growth factors such as eNOS or VEGF (97, 98). In addition, growth factors (such as granulocyte-macrophage colony-stimulating factor, erythropoietin and statins) that mobilize pro-angiogenic factors bone marrow stem cells and endothelial progenitor cells into the circulation (99) are also part of the invention.

Overexpression of extracellular matrix components in the CTO that are pro-angiogenic such as hyaluronan, fibronectin, perlecan, and/or versican, matrix metalloproteinases such as collagenase have been shown to enhance angiogenesis, suggesting combined therapy with collagenase can also be used as part of the present invention.

Inflammatory cells and mediators are also part of the present invention. Macrophages in particular have been shown to enhance angiogenesis. Macrophage colony stimulating factor (M-CSF) is a hematopoietic growth factor that induces survival, proliferation, differentiation and activation of mononuclear phagocytes and promotes angiogenesis (100). Also included are substances that cause activation of macrophages, chemotaxis of macrophages to the chronic total occlusion or local delivery of autologous activated macrophages previously obtained from peritoneal lavage fluid. In this procedure, already successfully performed in rats and rabbits, phosphate buffered saline is injected intra-peritonealy and collected after a waiting period of 20-30 minutes. Macrophages are isolated and grown in a specific culture (101).

Other approaches to administration of angiogenic agents of the invention, or to preparation thereof for such administration, are encompassed by the invention. Approaches in to administration thus include local or systemic injection of growth factors or pro-angiogenic substances as free substances or combined with other delivery methods. Local delivery methods include cell-based (eg fibroblast, smooth muscle cells, endothelial cell, endothelial progenitor cells or stem cells [isolated from embryos, or bone marrow or circulating blood of adults] that may or may not have been genetically engineered to overexpress angiogenic factors) or non-cell based delivery therapies such as naked DNA plasmids, viral vectors, nanoparticles, microsphere beads, polymer platforms, and intravascular stents. Examples of angiogenic polymer platforms include angiogenic Theramers (Rimon Therapeutics, Toronto, Canada). Theramers™ are medical polymers that have biological activity in and of themselves, without the use of drugs and are intended to used as solids (eg. Beads, scaffolds and coatings). Alternatively, angiogenic polymers can be locally delivered as soluble substances, incorporated into gels, or developed into other injectable formulations.

Different local delivery methods into the CTO are described and illustrated in WO 03/028756 published Apr. 10, 2003, and include over-the-wire ports in balloon angioplasty catheters, incorporated into stents directly onto stent struts or into covered stents or by other delivery devices.

The invention can be a kit made up of a pharmaceutical composition for inducing angiogenesis in an occlusion of an artery. The kit includes a first package containing an angiogenic agent and a second package containing a diluent. The contents of the packages are mixed to produce an angiogenic agent in a form suitable for immediate delivery through a catheter to a chronic total occlusion located in the artery of a human. Guidelines for pharmaceutical administration in general are provided in, for example, *Remington's Pharmaceutical Sciences* 18th *Edition,* Ed. Gennaro, Mack Publishing, 1990, and *Modern Pharmaceutics* 2nd *Edition,* Eds. Banker and Rhodes, Marcel Dekker, Inc., 1990, both of which are hereby incorporated by reference herein.

Mechanical methods to induce angiogenesis are known and are intended to be part of the present invention. Such methods include local catheter based cryotherapy (temperature range 10° C. to −50° C.). Direct application of the cryocatheter to the entrance of the CTO can enhance angiogenesis at that site (102). Similar effects can occur with various forms of local laser ablation against the entrance site of CTO (103)

In the case of peripheral CTOs, e.g., limbs, angiogenic agents can be delivered periadventitially by injection through a small incision, for example.

While describing specific combinations of elements, it is the intention of the inventors to include as part of this invention, other combinations of elements described herein as part of the invention.

REFERENCES

All references cited in this specification are incorporated herein by reference as though reproduced in their entirety herein.
1. Baim D S, Ignatius E J. Use of coronary angioplasty: Results of a current survey. Am J Cardiol 1988; 61:3G-8G
2. Noguchi T, Miyazaki S, Morii I, Daikoku S, Goto. Y, Nonogi H. Percutaneous transluminal coronary angioplasty of chronic total occlusions: determinants of primary success and long-term outcome. Cathet Cardiovasc Intervent 2000; 49:258-264
3. Ivanhoe R J, Weintraub W S, Douglas J S, et al. Percutaneous transluminal coronary angioplasty of chronic total occlusions: primary success, restenosis, and long-term clinical follow-up. Circulation 1992; 85:106-115
4. Dzavik V, Beanlands D S, Davies R F, Leddy D, Marquis J-F, Teo K K, Ruddy T D, Burton J R, Humen D P. Effects of late percutaneous transluminal coronary angioplasty of an occluded infarct-related coronary artery on left ventricular function in patients with a recent (<6 weeks) Q-wave acute myocardial infarction (Total Occlusion post-Myocardial Infarction Intervention Study [TOMIIS]—A pilot study. Am J Cardiol 1994; 73:856-61
5. Pizzetti G, Belotti G, Margonato A, Cappelletti A, Chierchia S. Coronary recanalization by elective angioplasty prevents ventricular dilatation after anterior myocardial infarction. J Am Coll Cardiol 1996; 28:837-45
6. Sirnes P A. Myreng Y. Molstad P. Bonarjee V. Golf S. Improvement in left ventricular ejection fraction and wall motion after successful recanalization of chronic coronary occlusions. Eur Heart J 1998; 19:273-81
7. Danchin N. Angioi M. Cador R. Tricoche O. Dibon O. Juilliere Y. Cuilliere M. Cherrier F. Effect of late percutaneous angioplastic recanalization of total coronary artery occlusion on left ventricular remodeling, ejection fraction, and regional wall motion. Am J Cardiol 1996; 78:729-35.
8. Lamas G A, Flaker G C, Mitchell G, et al. for the Survival Ventricular Enlargement Investigators. Effect of infarct artery patency on prognosis after acute myocardial infarction. Circulation 1995; 92:1101-1109.
9. Suero J A, Marso S P, Jones P G, et al. Procedural outcomes and long-term survival among patients undergoing percutaneous coronary intervention of a chronic total occlusion in native coronary arteries: a 20-year experience. J Am Coll Cardiol 2001; 38:409-14
10. Ramanathan K, Gao M, Nogareda G J, et al. Successful percutaneous recanalization of a non-acute occluded coronary artery predicts clinical outcomes and survival. Circulation 2001; 104:415A (abstract).
11. Srinivas V S, Borrks M M, Detre K M, et al. Contemporary percutaneous coronary intervention versus balloon angioplasty for multivessel coronary artery disease. A comparison of the National Heart, Lung, and Blood Institute Dynamic Registry and the Bypass Angioplasty Revascularization Investigation (BARI) study. Circulation 2002; 106:1627-1633
12. King S B, Lembo N J, Weintraub W S, et al., for the Emory Angioplasty versus Surgery Trial Investigators. A randomized trial comparing coronary angioplasty with coronary bypass surgery. N Engl J Med 1994; 331:1044-1050.
13. Stone G W, Rutherford B D, McConahay D R, Johnson W L Jr, Giorgi L V, Ligon R W, Hartzler G O. Procedural outcome of angioplasty for total coronary artery occlusion: an analysis of 971 lesions in 905 patients. J Am Coll Cardiol 1990; 15:849-56
14. Bell M R, Berger P B, Bresnahan J F, et al. Initial and long-term outcome of 354 patients after coronary balloon angioplasty of total coronary artery occlusions. Circulation 1992; 85:1003-11
15. Puma J A, Sketch M H, Tcheng J E, et al. Percutaneous revascularization of chronic coronary occlusions—an overview. J Am Coll Cardiol 1995; 26:1-11
16. Srivatsa S S, Edwards W D, Boos C M, Grill D E, Sangiorgi G M, Garratt K N, Schwartz R S, Holmes D R Jr. Histologic correlates of angiographic chronic total coronary artery occlusions: influence of occlusion duration on neovascular channel patterns and intimal plaque composition. J Am Coll Cardiol 1997; 29:955-63
17. Suzuki T, Hosokawa H, Yokoya K, et al. Time-dependent morphologic characteristics in angiographic chronic total coronary occlusions. Am J Cardiol 2001; 88:167-9.
18. Kwon H M, Sangiorgi G, Ritman E L, McKenna C, Holmes D R Jr, Schwartz R S, Lerman A. Enhanced coronary vasa vasorum neovascularization in experimental hypercholesterolemia. J Clin Invest. 1998; 101:1551-6.
19. Kwon H M, Sangiorgi G, Ritman E L, Lerman A, McKenna C, Virmani R, Edwards W D, Holmes D R, Schwartz R S. Adventitial vasa vasorum in balloon-injured coronary arteries: visualization and quantitation by a microscopic three-dimensional computed tomography technique. J Am Coll Cardiol. 1998; 32:2072-9.
20. Cheema A N, Hong T, Nili N, Moffat J G, Lipson K E, Howlett A R, Holdsworth D W, Cole M, Qiang B, Kolodgie F, Virmani R, Stewart D J, Strauss B H. Adventitial Angiogenesis: A novel mechanism of in-stent restenosis and inhibitory effects of SU11218, a tyrosine kinase inhibitor. J Am Coll Cardiol 2006 In press
21. De Martin R, Hoeth M, Hofer-Warbinek R, Schmid J A. The transcription factor NF-kappa B and the regulation of vascular cell function. Arterioscler Thromb Vasc Biol. 2000; 20:E83-8
22. Celletti F L, Waugh J M, Amabile P G et al. Vascular endothelial growth factor enhances atherosclerotic plaque progression. Nat Med 2001; 7(4):425-9

23. Celletti F L, Hilfiker P R, Ghafouri P, Dake M D. Effect of human recombinant vascular endothelial growth factor 165 on progression of atherosclerotic plaque. J Am Coll Cardiol 2001; 37:2126-30.
24. Moulton K S, Heller E, Konerding M A et al. Angiogenesis inhibitors endostatin or TNP-470 reduce intimal neovascularization and plaque growth in apolipoprotein E-deficient mice. Circulation 1999; 99:1726-32
25. Heeschen C, Jang J J, Weis M, Pathak A, Kaji S, Hu R S, Tsao P S, Johnson F L, Cooke J P. Nicotine stimulates angiogenesis and promotes tumor growth and atherosclerosis. Nat Med 2001; 7:833-9
26. de Boer O J, van der Wal A C, Teeling P, Becker A E. Leucocyte recruitment in rupture prone regions of lipid-rich plaques: a prominent role for neovascularization? Cardiovasc Res 1999; 41:443-9.
27. Jeziorska M, Woolley D E. Local neovascularization and cellular composition within vulnerable regions of atherosclerotic plaques of human carotid arteries. J Pathol 1999; 188:189-96
28. Dible H J. Organization and canalization in arterial thrombosis. J Pathol Bacteriol 1958; LXXV:1-7
29. Wakefield T W, Linn M J, Henke P K, Kadell A M, Wilke C A, Wrobleski S K, Sarkar M, Burdick M D, Myers D D, Strieter R M. Neovascularization during venous thrombosis organization: a preliminary study. Vasc Surg 1999; 30:885-92.
30. Burnand K G, Gaffney P J, McGuinness C L, Humphries J, Quarmby J W, Smith A. The role of the monocyte in the generation and dissolution of arterial and venous thrombi. Cardiovasc Surg 1998; 6:119-25
31. McGuinness C L, Humphries J, Waltham M, Burnand K G, Collins M, Smith A. Recruitment of labelled monocytes by experimental venous thrombi. Thromb Haemost 2001; 85:1018-24
32. Sevitt S. Organic canalisation and vascularisation of deep vein thrombi studied with dyed-micropaque injected at necropsy. J. Pathol. 1970; 100(2):I
33. Majno G, Joris I. Cell, tissues and disease. Principles of General Pathology. Cambridge, Blackwell Science, 1996.
34. Cox J L, Chiasson D A, Gotlieb A I. Stranger in a strange land: the pathogenesis of saphenous vein graft stenosis with emphasis on structural and functional differences between veins and arteries. Prog Cardiovasc Dis 1991; 34:45-68
35. Wong A P, Nili N, Strauss B H. Differences in Phenotypic Modulation, Proliferation and Matrix Protein Synthesis in Venous and Arterial-derived Smooth Muscle Cells: Potential Role of Decorin. Cardiovasc Res 2005; 65:702-10
36. Davies M J, Ballantine S J, Robertson W B, Woolf N. The ultrastructure of organising experimental mural thrombi in the pig aorta. J. Pathol. 1975; 117(2):75-81
37. Leu H J, Feigl W, Susani M. Angiogenesis from mononuclear cells in thrombi. Virchows Arch A Pathol Anat Histopathol 1987; 411:5-14.
38. Leu H J, Feigl W, Susani M, Odermatt B. Differentiation of mononuclear blood cells into macrophages, fibroblasts and endothelial cells in thrombus organization. Exp Cell Biol 1988; 56:201-10
39. Singh I, Burnand K G, Collins M, Luttun A, Collen D, Boelhouwer B, Smith A. Failure of thrombus to resolve in urokinase-type plasminogen activator gene-knockout mice: rescue by normal bone marrow-derived cells. Circulation 2003; 107:869-75
40. Rooney P, Kumar S. Inverse relationship between hyaluronan and collagens in development and angiogenesis. Differentiation 1993; 54:1-9
41. Ruoslahti E, Yamaguchi Y. Proteoglycans as modulators of growth factor activities. Cell 1991; 64:867-869
42. Ruoslahti E. Fibronectin and its integrin receptors in cancer. Adv Cancer Res. 1999; 76:1-20
43. Cai W J, Koltai S, Kocsis E, Scholz D, Kostin S, Luo X, Schaper W, Schaper J. Remodeling of the adventitia during coronary arteriogenesis. Am J Physiol Heart Circ Physiol 2003; 284:H31-40
44. Jiang X, Couchman J R. Perlecan and tumor angiogenesis. J Histochem Cytochem 2003; 51:1393-410.
45. Iozzo R V, San Antonio J D. Heparan sulfate proteoglycans: heavy hitters in the angiogenesis arena. J Clin Invest 2001; 108:349-55.
46. Segev A, Nili N, Strauss B H. The role of perlecan in arterial injury and angiogenesis. Cardiovascular Research 2004; 63:603-10
47. Zheng P S, Wen J, Ang L C, Sheng W, Viloria-Petit A, Wang Y, Wu Y, Kerbel R S, Yang B B. Versican/PG-M G3 domain promotes tumor growth and angiogenesis. FASEB J 2004; 18:754-6
48. Kroon M E, van Schie M L, van der Vecht B, van Hinsbergh V W, Koolwijk P. Collagen type 1 retards tube formation by human microvascular endothelial cells in a fibrin matrix. Angiogenesis 2002; 5:257-65
49. Davies Cde L, Melder R J, Munn L L, Mouta-Carreira C, Jain R K, Boucher Y. Decorin inhibits endothelial migration and tube-like structure formation: role of thrombospondin-1. Microvasc Res 2001; 62:26-42
50. Grant D S, Yenisey C, Rose R W, Tootell M, Santra M, Iozzo R V. Decorin suppresses tumor cell-mediated angiogenesis. Oncogene 2002; 21:4765-77
51. Liekens S, De Clercq E, Neyts J. Angiogenesis: regulators and clinical applications. Biochem Pharmacol 2001; 61:253-70
52. Sivakumar B, Harry L E, Paleolog E M. Modulating angiogenesis: more vs less. JAMA 2004; 292:972-7
53. Folkman J. Fundamental concepts of the angiogenic process. Curr Mol Med 2003; 3:643-51
54. Suri C, Jones P F, Patan S, et al. Requisite role of angiopoietin-1, a ligand for the TIE2 receptor, during embryonic angiogenesis. Cell 1996; 87:1171-80
55. Maisonpierre P C, Suri C, Jones P F, et al. Angiopoietin-2, a natural antagonist for Tie2 that disrupts in vivo angiogenesis. Science 1997; 277:55-60
56. Holash J, Maisonpierre P C, Compton D, et al. Vessel cooption, regression, and growth in tumors mediated by angiopoietins and VEGF. Science 1999; 284:1994-8.
57. Hellstrom M, Gerhardt H, Kalen M, et al. Lack of pericytes leads to endothelial hyperplasia and abnormal vascular morphogenesis. J Cell Biol 2001; 153:543-53
58. Abramsson A, Lindblom P, Betsholtz C. Endothelial and nonendothelial sources of PDGF-B regulate pericyte recruitment and influence vascular pattern formation in tumors. J Clin Invest 2003; 112:1142-51
59. Asahara T, Chen D, Takahashi T, et al. Tie2 receptor ligands, angiopoietin-1 and angiopoietin-2, modulate VEGF-induced postnatal neovascularization. Circulation Research 1998; 83:233-40
60. Kim I, Kim H G, Moon S O, et al. Angiopoietin-1 induces endothelial cell sprouting through the activation of focal adhesion kinase and plasmin secretion. Circ Res 2000; 86:952-9
61. Thurston G, Rudge J S, Ioffe E, et al. Angiopoietin-1 protects the adult vasculature against plasma leakage. Nat Med 2000; 6:460-3

62. Montesano R, Vassalli J D, Baird A, Guillemin R, Orci L. Basic fibroblast growth factor induces angiogenesis in vitro. Proc Natl Acad Sci USA 1986; 83:7297-301
63. Pepper M S. Transforming growth factor-beta: vasculogenesis, angiogenesis, and vessel wall integrity. Cytokine Growth Factor Rev 1997; 8:21-43
64. Babaei S, Teichert-Kuliszewska K, Zhang Q, Jones N, Dumont D J, Stewart D J. Angiogenic actions of angiopoietin-1 require endothelium-derived nitric oxide. Am J. Pathol. 2003; 162:1927-1936
65. Cooke J P. NO and angiogenesis. Atheroscler Suppl 2003; 4:53-60
66. Neufeld G, Cohen T, Gengrinovitch S, Poltorak Z. Vascular endothelial growth factor (VEGF) and its receptors. FASEB J 1999; 13:9-22
67. Zachary I, Mathur A, Yla-Herttuala S, et al. Vascular protection: A novel nonangiogenic cardiovascular role for vascular endothelial growth factor. Arterio Thromb Vasc Biol 2000; 20:1512-1520
68. Levy A P. Hypoxic Regulation of VEGF mRNA Stability by RNA-binding Proteins. Trends Cardiovasc Med 1998; 8:246-50
69. Shima D T, Adamis A P, Ferrara N, Yeo K T, Yeo T K, Allende R, Folkman J, D'Amore P A. Hypoxic induction of endothelial cell growth factors in retinal cells: identification and characterization of vascular endothelial growth factor (VEGF) as the mitogen. Mol Med 1995; 1:182-93
70. Shweiki D, Itin A, Soffer D, Keshet E. Vascular endothelial growth factor induced by hypoxia may mediate hypoxia-initiated angiogenesis. Nature 1992; 359:843-5
71. Namiki A, Brogi E, Kearney M, et al. Hypoxia induces vascular endothelial growth factor in cultured human endothelial cells. J Biol Chem 1995; 270:31189-95
72. Carmeliet P, Dor Y, Herbert J M, Fukumura D, Brusselmans K, Dewerchin M, Neeman M, Bono F, Abramovitch R, Maxwell P, Koch C J, Ratcliffe P, Moons L, Jain R K, Collen D, Keshert E, Keshet E. Role of HIF-1 alpha in hypoxia-mediated apoptosis, cell proliferation and tumour angiogenesis. Nature 1998; 394:485-90.
73. Mazure N M, Brahimi-Horn M C, Pouyssegur J. Protein kinases and the hypoxia-inducible factor-1, two switches in angiogenesis. Curr Pharm Des 2003; 9:531-41.
74. Shibuya M. Vascular endothelial growth factor receptor-2: its unique signaling and specific ligand, VEGF-E. Cancer Sci 2003; 94:751-6.
75. Waltham M, Burnand K G, Collins M, Smith A. Vascular endothelial growth factor and basic fibroblast growth factor are found in resolving venous thrombi. J Vasc Surg. 2000; 32:988-96
76. Waltham M, Burnand K G, Collins M, McGuinness C L, Singh I, Smith A. Vascular endothelial growth factor enhances venous thrombus recanalisation and organisation. Thromb Haemost 2003; 89:169-76
77. Fayad Z A and Fuster V. Clinical Imaging of High-risk or Vulnerable Atherosclerotic Plaque. Circ Res 2001 89:305-316
78. DeMarco J K, Rutt B K, Clarke S E. Carotid Plaque Characterization by Magnetic Resonance Imaging: Review of the Literature, Topics in Magnetic Resonance Imaging 2001; 12:205-217
79. Tofts P S, Modeling tracer kinetics in dynamic Gd-DTPA MR imaging, J Magn Reson Imaging 1997; 7:91-101.
80. Kellar K E, Fujii D K, Gunther W H, Briley-Saebo K, Bjornerud A, Spiller M, Koenig S H, NC100150 Injection, a preparation of optimized iron oxide nanoparticles for positive-contrast MR angiography, J Magn Reson Imaging 2000; 11:488-94
81. Bjornerud A, Johansson L O, Briley-Saebo K, Ahlstrom H K, Assessment of T1 and T2* effects in vivo and ex vivo using iron oxide nanoparticles in steady state—dependence on blood volume and water exchange, Magn Reson Med. 2002 March; 47(3):461-71
82. Marxen M, Thornton M M, Chiarot C B, Klement G, Koprivnikar J, Sled J G, Henkelman R M. MicroCT scanner performance and considerations for vascular specimen imaging. Med Phys 2004; 31:305-13
83. Flannery B, Dickman H, Roberge W, et al. Three dimensional x ray micro tomography. Science 1987; 237:1439-1444
84. Garcia-Sanz A, Rodriguez-Barbero A, Bentley M, et al. Three Dimensional Microcomputed Tomography of Renal Vasculature in Rats. Hypertension 1998; 31:440-444
85. Strauss B H, Goldman L, Qiang B. Nili N, Segev A, Butany J, Sparkes J D, Jackson Z S, Eskandarian M R, Virmani R. Collagenase plaque digestion for facilitating guide wire crossing in chronic total occlusions. Circulation 2003; 108:1259-62.
86. Segev A, Nili N, Qiang B. Charron T, Butany J, Strauss B H. Human-grade purified collagenase for the treatment of experimental arterial chronic total occlusion. Cardiovasc Revasc Med. 2005; 6:65-9.
87. Melchior J P, Meier B, Urban P, et al. Percutaneous transluminal coronary angioplasty for chronic total coronary arterial occlusion. Am J Cardiol 1988; 59:535-538.
88. Tsurumi Y, Takeshita S. Chen D, Kearney M, Rossow S T, Passeri J, Horowitz J R, Symes J F, Isner J M. Direct intramuscular gene transfer of naked DNA encoding vascular endothelial growth factor augments collateral development and tissue perfusion. Circulation 1996; 94:3281-90
89. Rutanen J, Rissanen T T, Markkanen J E, Gruchala M, Silvennoinen P, Kivela A, Hedman A, Hedman M, Heikura T, Orden M R, Stacker S A, Achen M G, Hartikainen J, Yla-Herttuala S. Adenoviral catheter-mediated intramyocardial gene transfer using the mature form of vascular endothelial growth factor-D induces transmural angiogenesis in porcine heart. Circulation. 2004; 109:1029-35
90. Gowdak L H, Poliakova L, Li Z, et al. Induction of angiogenesis by cationic lipid-mediated VEGF165 gene transfer in the rabbit ischemic hindlimb model. J Vasc Surg 2000; 32:343-352
91. Yla-Herttuala S, Alitalo K. Gene transfer as a tool to induce therapeutic vascular growth. Nat Med 2003; 9(6): 694-701.
92. Rosengart T K, Lee L Y, Patel S R, et al. Angiogenesis gene therapy: phase I assessment of direct intramyocardial administration of an adenovirus vector expressing VEGF121 cDNA to individuals with clinically significant severe coronary artery disease. *Circulation* 1999; 100:468-474.
93. Rosengart T K, Lee L Y, Patel S R, et al. Six-month assessment of a phase I trial of angiogenic gene therapy for the treatment of coronary artery disease using direct intramyocardial administration of an adenovirus vector expressing the VEGF121 cDNA. *Ann Surg* 1999; 230:466-470.
94. Schratzberger P, Schratzberger G, Silver M, et al. Favorable effect of VEGF gene transfer on ischemic peripheral neuropathy. Nat Med 2000; 6:405-413
95. Campbell A I, Zhao Y, Sandhu R, Stewart D J. Cell-based gene transfer of vascular endothelial growth factor attenuates monocrotaline-induced pulmonary hypertension. Circulation. 2001; 104:2242-8

96. Asahara T, Kawamoto A. Endothelial progenitor cells for postnatal vasculogenesis. Am J Physiol Cell Physiol. 2004; 287:C572-9
97. Iwaguro H, Yamaguchi J, Kalka C, Murasawa S, Masuda H, Hayashi S, Silver M, Li T, Isner J M, Asahara T. Endothelial progenitor cell vascular endothelial growth factor gene transfer for vascular regeneration. Circulation 2002; 105:732-8.
98. Zhao Y, Courtman D Y, Deng Y et al. Rescue of monocrotaline-induced pulmonary arterial hypertension using bone marrow-derived endothelial-like progenitor cells: efficacy of combined cell and eNOS gene therapy in established disease. Circ Res. 2005; 96:442-50.
99. Cho H J, Kim H S, Lee M M, et al. Mobilized endothelial progenitor cells by granulocyte-macrophage colony-stimulating factor accelerate reendothelialization and reduce vascular inflammation after intravascular radiation. Circulation. 2003; 108:2918-25
100. Eubank T D, Galloway M, Montague C M, Waldman W J, Marsh C B. M-CSF induces vascular endothelial growth factor production and angiogenic activity from human monocytes. J. Immunol. 2003; 171:2637-43.
101. Orenstein A, Kachel E, Zuloff-Shani A, Paz Y, Sarig O, Haik J, Smolinsky A K, Mohr R, Shinar E, Danon D. Treatment of deep sternal wound infections post-open heart surgery by application of activated macrophage suspension. Wound Repair Regen. 2005; 13:237-42.
102. Segev A, Strauss B H, Coates G, et al. Endocardial cryotherapy as a novel strategy of improving myocardial perfusion in a patient with severe coronary artery disease. Catheter Cardiovasc Interv 2003; 60:229-32.
103. Hughes G C, Biswas S S, Yin B et al. A comparison of mechanical and laser transmyocardial revascularization for induction of angiogenesis and arteriogenesis in chronically ischemic myocardium. J Am Coll Cardiol 2002; 39:1220-8.
104. Ellis S G, Shaw R E, Gershony G, et al. Risk factors, time course and treatment effect for restenosis after successful percutaneous transluminal coronary angioplasty of chronic total occlusion. Am J Cardiol 1989; 63:897-901.
105. Lefevre T, Louvard Y, Loubeyre C, et al. A randomized study comparing two guidewire strategies for angioplasty of chronic total coronary occlusion. Am J Cardiol 2000; 85:1144-7.
106. Kahler J, Koster R, Brockhoff C, et al. Initial experience with a hydrophilic-coated guidewire for recanalization of chronic coronary occlusions. Cathet Cardiovasc Interven 2000; 49:45-50

The invention claimed is:

1. A method of crossing through a chronic total occlusion with a guidewire during a percutaneous coronary intervention, which occlusion cannot be crossed through by a guide wire, the method comprising:
   (i) delivering an angiogenic agent to the occlusion site to promote angiogenesis within the occlusion;
   (ii) following step (i), waiting a period of time sufficient to increase susceptibility of the occlusion to crossing with the guidewire through angiogenesis within the occlusion; and
   (iii) following step (ii), crossing through the occlusion with the guidewire.

2. The method of claim 1, wherein the step of delivering the agent to the occlusion site includes bringing the agent into direct contact with the occlusion.

3. The method of claim 1, wherein delivering the angiogenic agent includes lodging a device within the vessel in the proximity of the occlusion, wherein the device is loaded with the agent and the agent is released therefrom over an extended period of time.

4. The method of claim 1, further comprising delivering a device into the vessel after the step of delivering the agent to retain the agent in direct contact with the occlusion for a period of time.

5. The method of claim 4, wherein the period of time is a predetermined period sufficient to induce angiogenesis in the occlusion.

6. The method of claim 5, wherein the period of time is between one day and ten weeks.

7. The method of claim 5, wherein the period of time is between seven and thirty days.

8. The method of claim 7, wherein the period of time is fourteen and twenty-eight days.

9. The method of claim 1 wherein the vessel is an artery of a human.

10. The method of claim 9, wherein the artery is located in the heart of the human, or the artery is a peripheral artery, or the artery is a femoral artery, or the artery is a popliteal artery, or the artery is a subclavian artery, or the artery is a brachial artery.

11. The method of claim 1, further comprising the step of monitoring the occlusion for the development of microvessels therein, subsequent to the delivery step.

12. The method of claim 11, wherein the monitoring step includes imaging the occlusion using magnetic resonance.

13. The method of claim 1, wherein the angiogenic agent is selected from the group of agents consisting of angiogenic growth factors, pro-angiogenic growth factors, cytokines, combinations of growth factors and/or cytokines, vascular endothelial growth factor, angiopoietin 1, angiopoietin 2, PDGF, FGF-2, TGF-beta, hepatocyte growth factor, TNF-alpha, endothelium-derived nitric oxide, nitric oxide donors, VEGFR-1, VEGFR-2, PDGFR, tie2, hypoxia inducible factor (HIF) 1-alpha, and combinations thereof.

14. The method of claim 13, wherein the angiogenic agent is vascular endothelial growth factor.

15. The method of claim 1, wherein the angiogenic agent is a stem cell that originates from an embryo or bone marrow or circulating blood of adults or endothelial progenitor cells (EPC).

16. The method of claim 15, wherein the angiogenic agent is a bone marrow stem cell.

17. The method of claim 1, further comprising the delivery of a growth factor selected from the group consisting of granulocyte-macrophage colony-stimulating factor, erythropoietin, statin and combinations thereof, so as to mobilize a pro-angiogenic factor into the circulation.

18. The method of claim 1, further comprising inducing overexpression of extracellular matrix components in the occlusion that are pro-angiogenic.

19. The method of claim 1, further comprising delivering a matrix metalloproteinase to the occlusion to enhance angiogenesis in the occlusion.

20. The method of claim 19, wherein the metalloproteinase is collagenase.

21. The method of claim 1, further comprising delivering macrophage colony stimulating factor (M-CSF) to the occlusion.

22. The method of claim 1, further comprising delivering a substance that causes activation of macrophages or chemotaxis of macrophages to the chronic total occlusion to the site of the occlusion.

23. The method according to claim 1, wherein the agent is delivered systemically.

24. The method according to claim 1, wherein the chronic total occlusion is located in a vessel and delivering the angiogenic agent includes inserting a delivery device containing the agent directly into the vessel to percutaneously deliver the agent directly to the site of the occlusion.

25. The method of claim 24, wherein the device includes a catheter, and the step of delivering the agent to the site of the occlusion includes conveying the agent through the catheter.

26. The method of claim 25, wherein the distal end of the catheter is brought within 10 cm of the occlusion prior to conveying the agent to the site through the catheter.

27. The method of claim 24, wherein the agent is delivered through the port of an over-the-wire device for delivering an angioplasty balloon.

28. The method of claim 1, wherein delivering the angiogenic agent includes lodging a device within the vessel in the proximity of the occlusion, wherein the device is loaded with the agent and the agent is released therefrom over an extended period of time of between 20 minutes and 40 minutes.

29. The method of claim 1, wherein delivering the angiogenic agent includes lodging a device within the vessel in the proximity of the occlusion, wherein the device includes a polymer loaded with the agent for release therefrom in use.

\* \* \* \* \*